United States Patent
Armour et al.

(10) Patent No.: US 6,914,160 B1
(45) Date of Patent: Jul. 5, 2005

(54) OXYTOCIN INHIBITORS

(75) Inventors: Duncan Robert Armour, Sandwich (GB); Andrew Simon Bell, Sandwich (GB); Paul John Edwards, Sandwich (GB); David Ellis, Sandwich (GB); David Hepworth, Sandwich (GB); Mark Llewellyn Lewis, Sandwich (GB); Christopher Ronald Smith, Sandwich (GB)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 10/632,438

(22) Filed: Jul. 31, 2003

Related U.S. Application Data
(60) Provisional application No. 60/432,787, filed on Dec. 11, 2002.

(30) Foreign Application Priority Data

Aug. 28, 2002 (GB) .............................................. 0219961

(51) Int. Cl.$^7$ .................... C07C 233/65; A61K 31/16
(52) U.S. Cl. .................... 564/158; 564/153; 549/366; 548/248; 548/374.1; 546/169; 546/304; 546/310; 544/297; 544/299; 544/300; 544/303; 544/355; 544/406; 514/249; 514/255; 514/269; 514/275; 514/311; 514/350; 514/378; 514/406; 514/456; 514/616
(58) Field of Search .......................... 514/249, 255, 514/269, 275, 311, 350, 378, 406, 456; 544/279, 300, 303, 355, 299, 406; 546/169, 304, 310; 548/248, 374.1; 549/366; 564/153, 158

(56) References Cited

U.S. PATENT DOCUMENTS

| | | | |
|---|---|---|---|
| 2,503,059 A | 4/1950 | Miescher et al. ......... | 260/309.6 |
| 2,599,000 A | 6/1952 | Kerwin et al. ........... | 260/570.7 |
| 3,381,009 A | 4/1968 | Palazzo ................... | 260/268 |
| 3,511,836 A | 5/1970 | Hess ....................... | 260/256.4 |
| 3,527,761 A | 9/1970 | Archibald et al. ........ | 260/293 |
| 3,997,666 A | 12/1976 | Witte et al. ............. | 424/250 |
| 4,026,894 A | 5/1977 | Winn et al. ......... | 260/256.4 Q |
| 4,188,390 A | 2/1980 | Campbell ................. | 424/251 |
| 4,252,721 A | 2/1981 | Silvestrini et al. ....... | 260/243.3 |
| 4,315,007 A | 2/1982 | Manoury ................. | 424/251 |
| 4,703,063 A | 10/1987 | Imai et al. ............... | 514/603 |
| 5,576,322 A | 11/1996 | Takase et al. ............ | 514/260 |
| 5,698,560 A | 12/1997 | Onoda et al. ............ | 514/267 |
| 5,945,117 A | 8/1999 | El-Rashidy et al. ..... | 424/430 |

FOREIGN PATENT DOCUMENTS

| | | | |
|---|---|---|---|
| EP | 0463756 | 1/1992 | ......... C07D/487/04 |
| EP | 0526004 | 2/1993 | ......... C07D/487/04 |
| EP | 0995750 | 4/2000 | ......... C07D/487/04 |
| EP | 0995751 | 4/2000 | ......... C07D/487/04 |
| EP | 1092718 | 4/2001 | ......... C07D/473/30 |
| EP | 1092719 | 4/2001 | ......... C07D/487/04 |
| EP | 1097719 | 5/2001 | ......... A61K/38/55 |
| WO | WO 9111172 | 8/1991 | ........... A61K/9/00 |
| WO | WO 9306104 | 4/1993 | ......... C07D/487/04 |
| WO | WO 9307149 | 4/1993 | ......... C07D/487/04 |
| WO | WO 9312095 | 6/1993 | ......... C07D/239/91 |
| WO | WO 9400453 | 1/1994 | ......... C07D/473/30 |
| WO | WO 9402518 | 2/1994 | ........... C08B/37/16 |
| WO | WO 9405661 | 3/1994 | ......... C07D/471/04 |
| WO | WO 9519978 | 7/1995 | ......... C07D/471/14 |
| WO | WO 9830560 | 7/1998 | ......... C07D/409/04 |
| WO | WO 9849166 | 11/1998 | ......... C07D/487/04 |
| WO | WO 9855148 | 12/1998 | ........... A61K/47/48 |
| WO | WO 9902159 | 1/1999 | ......... A61K/31/495 |
| WO | WO 9924433 | 5/1999 | ......... C07D/487/04 |
| WO | WO 9930697 | 6/1999 | ........... A61K/31/00 |
| WO | WO 9954333 | 10/1999 | ......... C07D/487/04 |
| WO | WO 0002550 | 1/2000 | ........... A61K/31/00 |
| WO | WO 0024745 | 5/2000 | ......... C07D/487/04 |
| WO | WO 0028993 | 5/2000 | ......... A61K/31/495 |
| WO | WO 0127112 | 4/2001 | ......... C07D/487/04 |
| WO | WO 0127113 | 4/2001 | ......... C07D/487/04 |

OTHER PUBLICATIONS

Pierre et al, J. Org. Chem, vol. 59, 1994, p. 1072–1077.*
Keating, et al., "Molecular Diversity via a Convertible Isocyanide in the Ugi Four–Component Condensation", *J. Am. Chem. Soc* 117, pp. 7842–7843 (1995).
Keating, et al., "Postcondensation Modifications of Ugi Four–Component Condensation Products: 1–isocyancyclohexene as a Convertible Isocyanide. Mechanism of Conversion, Synthesis of Diverse Structures, and Demonstration of Resin Capture", *J. Am. Chem. Soc.* 118, pp. 2574–2583 (1996).
Ley, et al., "A Ploymer–Supported [1,3,2]Oxazaphopholidine for the Conversion of Isothiocyanates to Isocyanides and Their Subsequent Use in an Ugi Reaction", *Bioorganic & Medicinal Chemistry Letters* 12, pp. 1813–1816 (2002).
Weber, et al., "An Improved Procedure for the Hofmann Carbylamine Sunthesis of Isonitriles", *Tetrahedron Letters* 17, pp. 1637–1640 (1972).
Melman, et al., "The Epidemiology and Pathophysiology of Erectile Dysfunction", *The Journal of Urology* 161, pp. 5–11 (1999).

(Continued)

*Primary Examiner*—Shailendra Kumar
(74) *Attorney, Agent, or Firm*—Peter C. Richardson; Gregg C. Benson; Martha G. Munchhof

(57) ABSTRACT

This invention relates to compounds of formula (I)

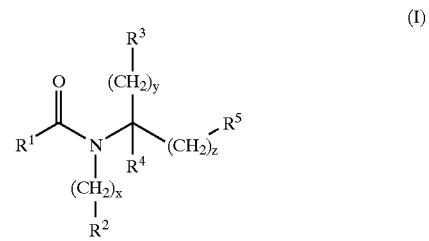

(I)

13 Claims, No Drawings

OTHER PUBLICATIONS

Rotella, et al., "N–3–Substituted Imidazoquinazolinones: Potent and Selective PDE5 Inhibitors as Potential Agents for Treatment of Erectile Dysfunction", *J. Med. Chem.* 43, pp. 1257–1263 (2000).

Mukalyama, et al., "The Deoxygenation of Isocyanates by 2–Phenyl–3–methyl–1,3,2–oxazaphospholidine. A Convenient Method for the Preparation of Isonitrilles", *Bulletin of the Chemical Society of Japan* 38(5), pp. 858–859 (1965).

Berge, et al., "Pharmaceutical Salts", *Journal of Pharmaceutical Sciences* 66(1), pp. 1–19 (1977).

Ugl, et al., "New Methods in Preparative Organic Chemistry IV", *Angew. Chemie Int. Edition* 4(6), pp. 472–484 (1965).

Creedon, et al., "Dehydration of Formamides Using the burgess Reagent: A New Route to Isocyandes", *J. Chem. Soc., Perkin Trans. 1*, pp. 1015–1017 (1998).

* cited by examiner

OXYTOCIN INHIBITORS

This application claims Priority from Great Britain Application No. 02199601.0 filed on Aug. 28, 2002 and U.S. provisional application Ser. No. 60/432,787 filed Dec. 11, 2002.

The present invention relates to a class of substituted amides with activity as Oxytocin inhibitors, uses thereof, processes for the preparation thereof and compositions containing said inhibitors. These inhibitors have utility in a variety of therapeutic areas including sexual dysfunction, particularly premature ejaculation (P.E.).

The present invention provides for compounds of formula (I)

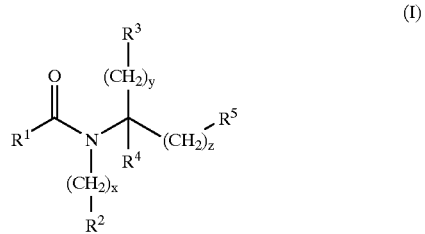

wherein:

$R^1$ is selected from:
  a) phenyl, which is optionally substituted by 1–3 groups each independently selected from $C_1$-$C_6$alkyl, $CF_3$, halo, CN, NR $R^8$, $OCF_3$, $SOR^6$, $SO_2R^6$ and $OC_1$-$C_6$ alkyl, wherein said alkyl group may be optionally substituted by a $C_3$-$C_8$ cycloalkyl group, and
  b) Aromatic Heterocycle, which is optionally substituted by 1–3 groups each independently selected from $C_1$-$C_6$ alkyl, $NH_2$, $CF_3$, halo, OH, $OC_1$-$C_6$ alkyl, $SR^6$, $SOR^6$, $SO_2R^6$, $NR^7R^8$ wherein $R^8$ may be optionally substituted by $NH_2$, phenyl or Heterocycle, and OPh wherein Ph may be optionally substituted by 1–3 groups each independently selected from halo and $C_1$-$C_6$ alkyl;

$R^2$ is selected from:
  a) phenyl, which is optionally substituted by $C_1$-$C_6$ alkyl, halo, CN, $NR^7R^8$, $OC_1$-$C_6$ alkyl, $OCF_3$, $CF_3$ and $SO_2R^6$,
  b) OPh, which is optionally substituted by $C_1$-$C_6$ alkyl, halo, $OC_1$-$C_6$alkyl, $OCF_3$, $CF_3$ and $SO_2R^6$,
  c) $C_3$-$C_8$ cycloalkyl which is optionally fused to phenyl,
  d) Aromatic Heterocycle,
  e) $R^6$,
  f) $C(O)NR^6R^6$, and
  g) Heterocycle, which is optionally substituted by $C(O)R^6$;

$R^3$ is selected from:
  a) phenyl, said phenyl being optionally fused to Heterocycle and said phenyl or said fused phenyl being optionally substituted by 1–3 groups each independently selected from: $C_1$-$C_6$alkyl, $CF_3$, halo, CN, $OCF_3$, $SO_2R^6$ and $OC_1$-$C_6$alkyl,
  b) Heterocycle,
  c) $R^6$,
  d) 3–8 membered cycloalkyl group, which is optionally substituted by $C_1$-$C_6$ alkyl, and
  e) Aromatic Heterocycle, which is optionally substituted by $C_1$-$C_6$ alkyl;

$R^4$ is hydrogen or $CH_3$;

$R^5$ is selected from:
  a) $CONH_2$, $CONHR^6$, $CONR^6R^6$, $R^6$, $NH_2$, $NHR^6$, OH, $OR^6$, $OC(O)NHR^6$, NHC(O)H, $NHC(O)R^6$, and
  b) Aromatic Heterocycle, which is optionally substituted by 1–3 groups each independently selected from $C_1$-$C_6$alkyl, $NH_2$, $CF_3$, halo, $SR^6$, OH, $OC_1$-$C_6$ alkyl, $NHR^6$ wherein the $R^6$ moiety may be optionally substituted by phenyl or Heterocycle, and OPh wherein Ph may be optionally substituted by 1–3 groups each independently selected from halo and $C_{1-4}$ alkyl;

$R^6$ is $C_{1-6}$ alkyl;
$R^7$ is hydrogen or $C_1$-$C_6$ alkyl;
$R^8$ is $C_1$-$C_6$ alkyl;
or $NR^7R^8$ forms a monocyclic saturated ring system containing between 3 and 7 ring atoms;
x is 0, 1 or 2,
y is 0, 1 or 2, and
z is 0, 1 or 2, and
wherein:
Aromatic Heterocycle may be defined as a 5–6 membered aromatic heterocycle containing 1–4 heteroatoms each independently selected from N, O and S, said ring optionally fused with a phenyl or a 3–8 membered cycloalkyl group;
Heterocycle is a 5–8 membered saturated or partially saturated ring containing 1–3 heteroatoms each independently selected from N, O and S, said ring optionally fused with phenyl.

The pharmaceutically acceptable salts of the compounds of the formula (I) include the acid addition and the base salts thereof.

A pharmaceutically acceptable salt of a compound of the formula (I) may be readily prepared by mixing together solutions of a compound of the formula (I) and the desired acid or base, as appropriate. The salt may precipitate from solution and be collected by filtration or may be recovered by evaporation of the solvent.

Suitable acid addition salts are formed from acids which form non-toxic salts and examples are the hydrochloride, hydrobromide, hydroiodide, sulphate, bisulphate, nitrate, phosphate, hydrogen phosphate, acetate, maleate, fumarate, lactate, tartrate, citrate, gluconate, succinate, saccharate, benzoate, methanesulphonate, ethanesulphonate, benzenesulphonate, p-toluenesulphonate and pamoate salts.

Suitable base salts are formed from bases which form non-toxic salts and examples are the sodium, potassium, aluminium, calcium, magnesium, zinc and diethanolamine salts.

For a review on suitable salts see Berge et al, J. Pharm. Sci., 66, 1–19, 1977.

The pharmaceutically acceptable solvates of the compounds of the formula (I) include the hydrates thereof.

Also included within the present scope of the compounds of the formula (I) are polymorphs thereof.

Also included within the present scope of the compounds of the formula (I) are atropisomers thereof.

A compound of the formula (I) contains one or more asymmetric carbon atoms and therefore exists in two or more stereoisomeric forms. Where a compound of the formula (I) contains an alkenyl or alkenylene group, cis (Z) and trans (E) isomerism may also occur. The present invention includes the individual stereoisomers of the compounds of the formula (I) and, where appropriate, the individual tautomeric forms thereof, together with mixtures thereof.

Separation of diastereoisomers or cis and trans isomers may be achieved by conventional techniques, e.g. by fractional crystallisation, chromatography or H.P.L.C. of a stereoisomeric mixture of a compound of the formula (I) or a suitable salt or derivative thereof. An individual enantiomer of a compound of the formula (I) may also be prepared from a corresponding optically pure intermediate or by resolution, such as by H.P.L.C. of the corresponding racemate using a suitable chiral support or by fractional crystallisation of the diastereoisomeric salts formed by reaction of the corresponding racemate with a suitable optically active acid or base, as appropriate.

Unless otherwise indicated, an alkyl or alkoxy group may be straight or branched and contain 1 to 8 carbon atoms, preferably 1 to 6 and particularly 1 to 4 carbon atoms. Examples of alkyl include methyl, ethyl, n-propyl, isopropyl, n-butyl, isobutyl, sec-butyl, pentyl and hexyl. Examples of alkoxy include methoxy, ethoxy, isopropoxy and n-butoxy.

Unless otherwise indicated, a cycloalkyl or cycloalkoxy group may contain 3 to 10 ring-atoms, may be either monocyclic or, when there are an appropriate number of ring atoms, polycyclic. Examples of cycloalkyl groups are cyclopropyl, cyclopentyl, cyclohexyl and adamantyl.

Examples of Aromatic Heterocycle are furyl, thienyl, pyrrolyl, oxazolyl, thiazolyl, imidazolyl, pyrazolyl, isoxazolyl, isothiazolyl, oxadiazolyl, triazolyl, thiadiazolyl, pyridyl, pyrimidinyl, pyrazinyl, pyridazinyl, tetrazolyl, triazinyl. In addition, the term heteroaryl includes fused heteroaryl groups, for example benzimidazolyl, benzoxazolyl, imidazopyridinyl, benzoxazinyl, benzothiazinyl, oxazolopyridinyl, benzofuranyl, quinolinyl, quinazolinyl, quinoxalinyl, benzothiazolyl, phthalimido, benzofuranyl, benzodiazepinyl, indolyl and isoindolyl.

Examples of Heterocycle are oxiranyl, azetidinyl, tetrahydrofuranyl, thiolanyl, pyrrolidinyl, pyrrolinyl, imidazolidinyl, imidazolinyl, sulfolanyl, dioxolanyl, dihydropyranyl, tetrahydropyranyl, piperidinyl, pyrazolinyl, pyrazolidinyl, dioxanyl, morpholinyl, dithianyl, thiomorpholinyl, piperazinyl, azepinyl, oxazepinyl, thiazepinyl, thiazolinyl and diazapanyl.

Halo means fluoro, chloro, bromo or iodo.

Unless otherwise indicated, the term substituted means substituted by one or more defined groups. In the case where groups may be selected from a number of alternative groups, the selected groups may be the same or different.

Preferably $R^1$ is selected from:
a) phenyl, which is optionally substituted by 1–3 groups each independently selected from $C_1$-$C_6$alkyl, $CF_3$, halo, CN, $NR^7R^8$, $SO_2R^6$ and $OC_1$-$C_6$ alkyl, and
b) Aromatic Heterocycle, wherein said Aromatic Heterocycle is selected from pyridyl, pyrazinyl, pyrimidinyl, quinolinyl, quinoxalinyl, isoxazolyl and pyrazolyl, each aromatic heterocycle optionally substituted by 1–3 groups each independently selected from $C_1$-$C_6$ alkyl, $SR^6$, $SO_2R^6$, $NH_2$, $CF_3$, halo, OH, $OC_1$-$C_6$ alkyl, $NR^7R^8$ wherein $R^8$ may be optionally substituted by $NH_2$, phenyl or Heterocycle, and OPh wherein Ph may be optionally substituted by 1–3 groups each independently selected from halo and $C_1$–$C_6$alkyl.

More preferably $R^1$ is selected from:
a) phenyl, which is optionally substituted by 1–3 groups each independently selected from $C_1$-$C_6$ alkyl, $CF_3$, halo, CN, $NR^7R^8$, $SO_2R^6$ and $OC_1$-$C_6$ alkyl, and
b) Aromatic Heterocycle, wherein said Aromatic Heterocycle is selected from:
i) pyridyl, which is optionally substituted by 1–3 groups each independently selected from $C_1$-$C_6$ alkyl, $SO_2R^6$, $NH_2$, $CF_3$, CN, halo, OH, $OC_1$-$C_6$alkyl, $NR^7R^8$ wherein $R^8$ may be optionally substituted by $NH_2$, phenyl or Heterocycle, and OPh wherein Ph may be optionally substituted by 1–3 groups each independently selected from halo and $C_1$-$C_6$alkyl;
ii) pyrimidinyl, which is optionally substituted by 1–3 groups each independently selected from $C_1$-$C_6$alkyl, $SO_2R^6$, $NH_2$, $CF_3$, CN, halo, OH, $OC_1$-$C_6$alkyl, $NR^7R^8$ wherein $R^8$ may be optionally substituted by $NH_2$, phenyl or Heterocycle, and OPh wherein Ph may be optionally substituted by 1–3 groups each independently selected from halo and $C_1$-$C_6$alkyl;
iii) pyrazinyl, which is optionally substituted by 1–3 groups each independently selected from $C_1$-$C_6$ alkyl, $NH_2$, $SR^6$ and halo;
iv) quinolinyl;
v) quinoxalinyl, which is optionally substituted by OH;
vi) isoxazolyl, which is optionally substituted by 1–3 groups each independently selected from: $C_1$-$C_6$alkyl; and
vii) pyrazole.

Yet more preferably $R^1$ is phenyl, 2- or 3-pyridyl or 2,4-pyrimidinyl, said moieties being optionally substituted by 1–3 groups each independently selected from $C_1$-$C_6$alkyl, halo, $OC_1$-$C_6$ alkyl, CN, $SO_2R^6$, $NHR_7$, $NHCH_2CH_2NH_2$ and $CF_3$.

Most preferably $R^1$ is phenyl, 2- or 3-pyridyl or 2,4-pyrimidinyl, said moieties being optionally substituted by 1–3 groups each independently selected from methyl, fluoro, chloro, methoxy, ethoxy, n-propoxy, CN, $SO_2CH_3$, $NH_2$, $NHCH_3$, $NHCH_2CH_2NH_2$, and $CF_3$.

Preferably $R^2$ is selected from:
a) phenyl, which is optionally substituted by $C_1$-$C_6$ alkyl, halo, $OC_1$-$C_6$alkyl, $OCF_3$, $NR^7R^8$, $CF_3$ or $SO_2R^6$,
b) OPh, which is optionally substituted by $C_1$-$C_6$ alkyl or halo,
c) cyclopropyl or 1- or 2-indanyl,
d) pyrazolyl, which is optionally substituted by $R^6$,
e) $R^6$,
f) $C(O)N(CH_3)_2$, and
g) 5–6 membered saturated ring containing 1 nitrogen atom, said ring being substituted by $C(O)R^6$;

More preferably $R^2$ is selected from:
a) phenyl, which is optionally substituted by methyl, halo, methoxy, $CF_3$ or $SO_2CH_3$,
b) cyclopropyl or 1- or 2-indanyl,
c) pyrazolyl, which is optionally substituted by methyl,
d) $C(O)N(CH_3)_2$, and
e) piperidinyl substituted by $C(O)R^6$;

Yet more preferably $R^2$ is selected from:
a) phenyl, which is optionally substituted by methyl, fluoro, chloro, methoxy, $CF_3$ or $SO_2CH_3$,
b) pyrazolyl, which is optionally substituted by methyl, and
c) $C(O)N(CH_3)_2$.

Most preferably $R^2$ is phenyl, para-fluorophenyl, para-chlorophenyl, para-methylphenyl, 2,5-dimethylphenyl, o-methylphenyl and para-methoxyphenyl.

Preferably $R^3$ is selected from:
a) phenyl, said phenyl being optionally fused to Heterocycle and said phenyl or said fused phenyl being optionally substituted by 1–3 groups each independently selected from $C_1$-$C_6$ alkyl, halo, CN and $OC_1$-$C_6$ alkyl, b) $R^6$, c) cyclopropyl, cyclobutyl, cyclopentyl or cyclohexyl, which is optionally substituted by $C_1$-$C_6$ alkyl; and d) Aromatic Heterocycle, wherein said Aromatic Heterocycle may be defined as a 5–6 membered aromatic heterocycle containing 1 or 2 nitrogen atoms, said ring optionally fused with a phenyl or a 3–8 membered cycloalkyl group.

More preferably $R^3$ is selected from:

a) phenyl, said phenyl being optionally fused to 1,4-dioxan and said phenyl or said fused phenyl being optionally substituted by 1–3 groups each independently selected from $C_1$-$C_6$ alkyl, halo, CN and $OC_1$-$C_6$ alkyl;

b) $R^6$, c) cyclopropyl, which is optionally substituted by $C_1$-$C_6$ alkyl; and d) Aromatic Heterocycle, wherein said Aromatic Heterocycle is selected from pyrazolyl or pyridyl, both optionally substituted by $C_1$-$C_6$ alkyl.

Yet more preferably $R^3$ is selected from:

a) phenyl, said phenyl being optionally fused to 1,4-dioxan and said phenyl or said fused phenyl being optionally substituted by 1–2 groups each independently selected from methyl, methoxy, ethoxy, fluoro, chloro and CN;

b) isopropyl;

c) cyclopropyl; and d) pyrazolyl and pyridyl, both optionally substituted by methyl.

Most preferably $R^3$ is selected from 3-methoxyphenyl and 1,4-benzodioxanyl.

Preferably $R^4$ is H.

Preferably $R^5$ is selected from: $CONH_2$, $CONHR^6$, $CONR^6R^6$ and $R^6$;

More preferably $R^5$ is $CONH_2$ or $CH_3$.

Most preferably $R^5$ is $CONH_2$.

Preferably $R^6$ is methyl.

Preferably x is 1.

Preferably y is 0.

Preferably z is 0 or 1.

Most preferably z is 0.

Preferably, Aromatic Heterocycle may be defined as a 5–6 membered aromatic heterocycle containing 1–3 heteroatoms each independently selected from N, O and S, said ring optionally fused with a phenyl or a 3–8 membered cycloalkyl group.

More preferably, Aromatic Heterocycle may be defined as a 5–6 membered aromatic heterocycle containing 1–2 heteroatoms each independently selected from N, O and S, said ring optionally fused with a phenyl.

Preferably, Aromatic Heterocycle is selected from pyridyl, pyrazinyl, pyrimidinyl, quinolinyl, quinoxalinyl, isoxazolyl and pyrazolyl.

Heterocycle is a 5–8 membered saturated or partially saturated ring containing 1–3 heteroatoms each independently selected from N, O and S, said ring optionally fused with phenyl.

Preferably, Heterocycle is a 5–6 membered saturated ring containing 1–3 heteroatoms each independently selected from N, O and S.

Preferably, Heterocycle is a 5–6 membered saturated ring containing 1 nitrogen atom.

All of the above reactions and the preparations of novel starting materials using in the preceding methods are conventional and appropriate reagents and reaction conditions for their performance or preparation as well as procedures for isolating the desired products will be well-known to those skilled in the art with reference to literature precedents and the Examples and Preparations hereto.

Compounds of formula (I) where $R^1$, $R^2$, $R^3$ and y are as described above, x is 1, z is 0, $R^4$ is H and $R^5$ is $CONH_2$ may be prepared by the following process as described in Scheme 1:

Scheme 1

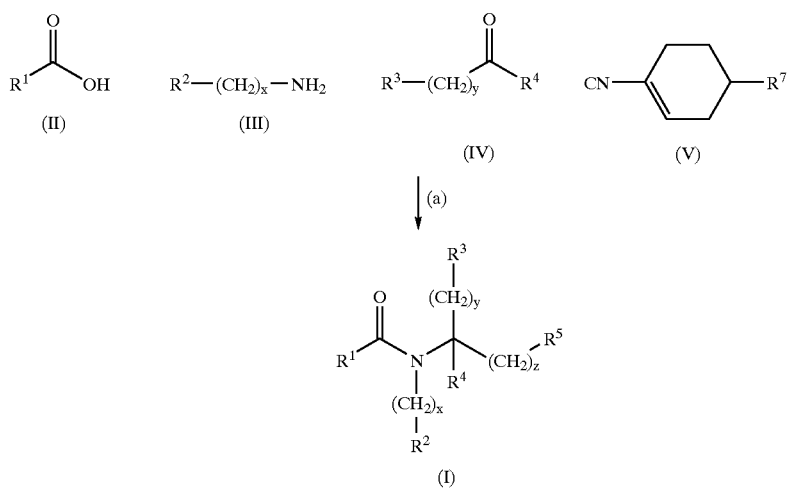

Compounds of formula (I) may be prepared by reacting compounds of formula (II), (III), (IV) and (V), where $R^7$ may be H or Ph, under the conditions of process step (a) Ugi 4 component condensation—the acid, amine, aldehyde and isonitrile are reacted together to give the desired compounds using the method of Keating, T. A. and Armstrong, R. W., J. Am. Chem. Soc. (1995), 117(29), 7842-3.

Typically—the acid, amine, aldehyde and isonitrile are stirred together in a suitable solvent such as methanol, ethanol, THF, $Et_2O$, DME, DMF, DMSO at a temperature of 0°C to the reflux temperature of the solvent for 1–48 hours. The mixture is then treated with an acid such as HCl, $H_2SO_4$, AcOH in a suitable solvent such as methanol, ethanol, THF, Et$_2$O, DME, DMF, DMSO at a temperature of 0°C to the reflux temperature of the solvent for an additional 1–48 hours.

Preferably—a mixture of the acid, 1.1 equivalents of the amine and 1.0 equivalents of the aldehyde in methanol was treated with 1.0 equivalents of (4-isocyano-3-cyclohexen-1-yl)-benzene (Baldwin, J. E.; O'Neil, I. A. Tetrahedron Lett. (1990), 31(14), 2047-50) and the mixture was stirred at room temperature for 18 hours. The mixture was then heated to 50°C for 4 hours. The cooled mixture was treated with cHCl in THF (7% by volume) and stirred at room temperature for another 18 hours.

Compounds of formula (VI) and (VII) are also produced as by products of process step (a)

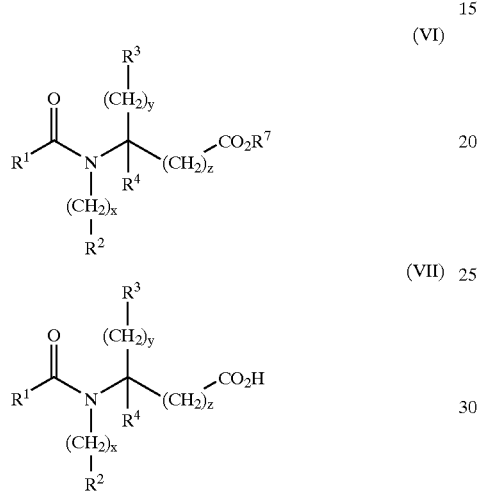

Compounds of formula (VI) may be converted into compounds of formula (VII) and subsequently transformed into compounds of formula (I).

It will be understood by one skilled in the art, that the Ugi 4 component condensation sometimes forms the acid (VII) directly without the intermediacy of the ester (VI). This is believed to be due to the formation of a münchnone intermediate which is trapped by water, Keating, T. A.; Armstrong, R. W. J. Am. Chem. Soc. (1996) 118, 2574. The relative proportions depend primarily upon the starting materials used. However, certain conditions may be used in process step (a) to increase the relative proportions of (VII) to (VI):

Typically—the acid, amine, aldehyde and isonitrile are stirred together in a suitable solvent such as methanol, ethanol, THF, Et$_2$O, DME, DMF, DMSO at a temperature of 0°C to the reflux temperature of the solvent for 1–48 hours. The mixture is treated with an acid such as HCl, H$_2$SO$_4$, AcOH or acid chloride such as acetyl chloride in a suitable alcoholic solvent such as MeOH or EtOH, the choice of alcohol dictating the ester that is ultimately formed Preferably—a mixture of the acid, 1.1 equivalents of the amine and 1.0 equivalents of the aldehyde in methanol was treated with 1.0 equivalents of the isonitrile and the mixture was stirred at room temperature for 18 hours. The mixture was then heated to 50°C for 4 hours. The mixture is treated with 5.0 equivalents of acetyl chloride and heating continued for 4 hours.

As discussed above, compounds of formula (I) where R$^1$, R$^2$ and R$^3$ are as described above, x is 1, y is 0, z is 0, R$^4$ is H and R$^5$ is CONHR$^6$ or CONH$_2$ may be prepared from compounds of formula (VI) and (VII) by the following process as described in Scheme 2:

Scheme 2

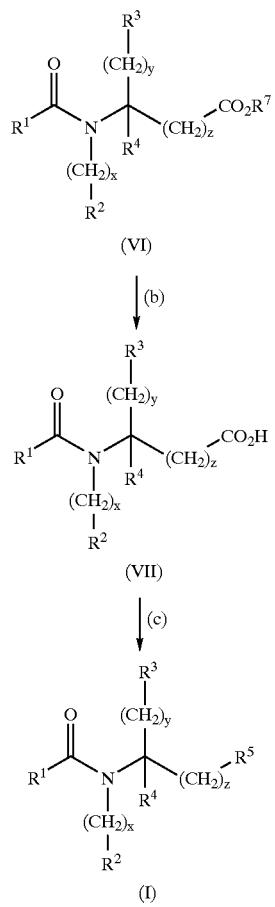

Compounds of formula (VII) may be prepared by reacting compounds of formula (VI), under the conditions of process step (b) Ester hydrolysis—the ester can be treated with either an acid or a base, with heating in a suitable solvent to effect the hydrolysis. Alternatively, if R$^7$=benzyl, the ester can be removed by hydrogenolysis using an appropriate catalyst.

Typically—the ester is treated with a metal hydroxide (Li, Na, K) in an aqueous solvent, MeOH, EtOH, THF, dioxan at a temperature of 0° C. to the reflux temperature of the solvent for 1–48 hours.

Preferably—a methanolic solution of the ester was stirred at room temperature for 18 hours in the presence of approximately 3 equivalents of aqueous sodium hydroxide.

Compounds of formula (I) may be prepared by reacting compounds of formula (VII), under the conditions of process step (c) Amide bond formation—such reactions may be carried out under a wide variety of conditions well known to the skilled man.

Typically—the carboxylic acid may be activated by treatment with an agent such as CDI, TFFH, or a combination of reagents such as PyAOP and HOAt, or by the intermediacy of the acid chloride, for example prepared by the use of oxalyl chloride and catalytic DMF. Alternatively, the reaction may be carried out by the addition of a peptide coupling agent such as HATU, or HBTU, or DCC or DIC to a mixture of the acid and amine. The reaction is carried out in a suitable solvent such as DCM, pyridine, DMF, DMA or NMP at a temperature of 0°C to the reflux temperature of the solvent.

Preferably—equimolar amounts of the acid and amine, 1.1 equivalents of HBTU and 2–4 equivalents of DIPEA in DMF were stirred at room temperature for 18 hours.

Compounds of formula (I) where $R^1$, $R^2$, $R^3$ and y are as described above, x is 1, z is 0, $R^4$ is H and $R^5$ is $CONHR^6$ may be prepared by the following process as described in Scheme 3:

Scheme 3

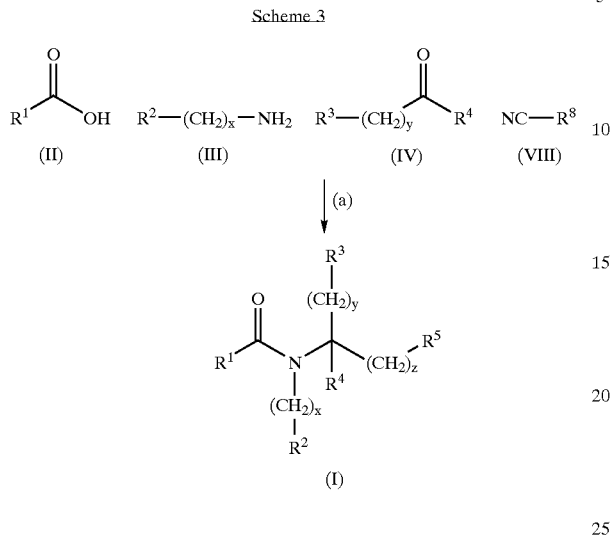

Scheme 3

Compounds of formula (I) may be prepared by reacting compounds of formula (II), (III), (IV) and (VIII), where $R^8$ may be H or Ph, under the conditions of process step (a) Ugi 4 component condensation as described herein.

Typically—the acid, amine, aldehyde and isonitrile are stirred together in a suitable solvent such as methanol, ethanol, THF, $Et_2O$, DME, DMF, DMSO at a temperature of 0°C to the reflux temperature of the solvent for 1–48 hours.

Preferably—a mixture of the acid, 1.1 equivalents of the amine and 1.0 equivalents of the aldehyde in methanol was treated with 1.0 equivalents of the isonitrile and the mixture was stirred at room temperature for 18 hours. The mixture was then heated to 50°C for 4 hours.

A variety of methods are obvious to one skilled in the art for the preparation of isonitriles of formula (VIII). For example the isothiocyanate can be converted into the corresponding isonitrile using 3-methyl-2-phenyl-[1,3,2]oxazaphospholidine according to the method of Mukaiyama, T; Yokota, Y. Bull. Chem. Soc. Jpn., (1965) 38, 858 or the polymer-supported equivalent of Ley, S. V.; Taylor, S. J., Bioorg. Med. Chem. Lett. (2002) 12(14), 1813. Alternative preparations of isonitriles include the methods of Weber, W. P.; Gokel, G. W., Tet. Lett. (1972) 1637, of Ugi, I Angew. Chem. Int. Ed. Engl. (1965) 4, 472 and of Creedon, S. M. et al, J. Chem. Soc. Perkin Trans. 1 (1998), 1015.

Compounds of formula (I) where $R^1$, $R^2$, $R^3$, $R^4$, z and y are as described above, x is 1 and $R^5$ is $CONR^6R^6$ may be prepared by the following process as described in Scheme 4:

Scheme 4

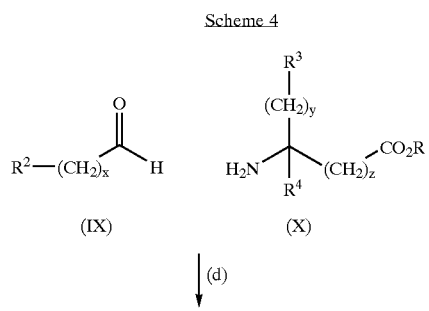

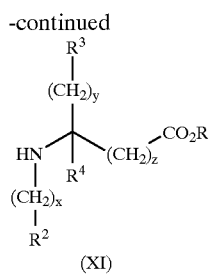

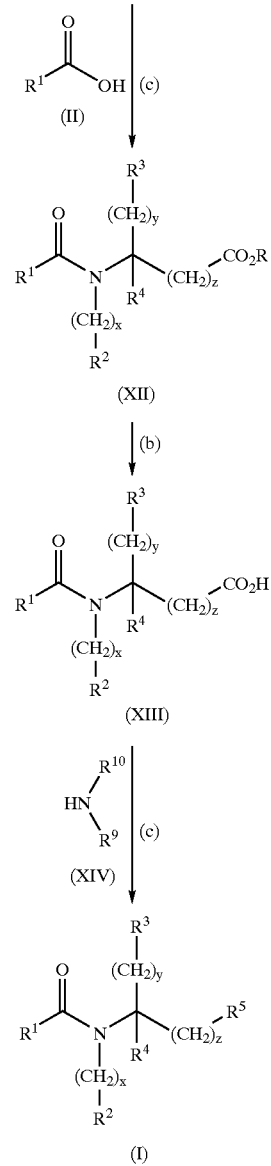

Compounds of formula (XI) may be prepared by reacting compounds of formula (IX) and (X), under the conditions of process step (d) Reductive amination—dehydration of an amine and aldehyde followed by reduction of the imine so formed, by a suitable metal hydride reducing agent, usually requiring Lewis acid catalysis in a suitable solvent at room temperature Typically—the amine and aldehyde are mixed together in a suitable solvent such as methanol, ethanol, THF, $Et_2O$, DCM or DCE and are treated with a suitable reducing agent, such as sodium triacetoxyborohydride or sodium cyanoborohydride and a catalytic quantity of acetic acid, and then stirred at room temperature for 1–48 hours. Alternatively, the amine and aldehyde are premixed for a time of 1–24 hours in a suitable solvent such as methanol, ethanol, THF, Et$_2$O, DCM or DCE, followed by the reducing agent such as sodium borohydride, sodium triacetoxyborohydride, sodium cyanoborohydride or lithium aluminium hydride and stirring continued for 1–48 hours at a temperature of 0□C to the reflux temperature of the solvent.

Preferably—a mixture of the amine, 1.05 equivalents of the aldehyde and 1.3 equivalents of sodium triacetoxyborohydride in DCM and catalytic acetic acid was stirred at room temperature for 18 hours.

Compounds of formula (XII) may be prepared by reacting compounds of formula (XI), under the conditions of process step (c) Amide bond formation as described herein.

Preferably—a mixture of the acid and 2.0 equivalents of oxalyl chloride with catalytic DMF in DCM was stirred at 0° C. for 2 hours. The solvent was removed in vacuo and the resultant crude acid chloride treated with 1.0 equivalents of the amine and 4 equivalents of DIPEA in DCM stirring at room temperature for 18 hours.

Compounds of formula (XIII) may be prepared by reacting compounds of formula (XII), under the conditions of process step (b) Ester hydrolysis as described herein.

Compounds of formula (I) may be prepared by reacting compounds of formula (XIV), where $R^9$ and $R^{10}$ are $C_{1-6}$ alkyl, or may link together to form a $C_{4-7}$ containing nitrogen heterocycle, and (XIII), under the conditions of process step (c) Amide bond formation as described herein.

Compounds of formula (I) where $R^1$, $R^2$, $R^3$, $R^4$, z and y are as described above, x is 1 and $R^5$ is $CONR^6R^6$ may be prepared by the following process as described in Scheme 5:

Scheme 5

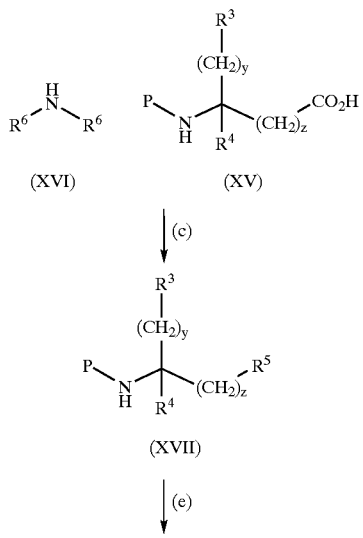

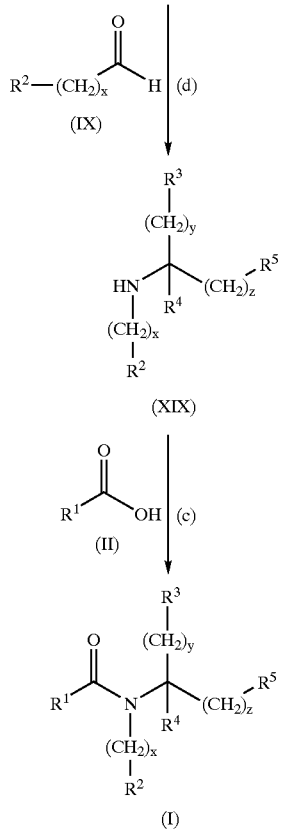

Compounds of formula (XVII) may be prepared by reacting compounds of formula (XVI), where $R^6$ is as defined herein, and (XV), where P is a suitable nitrogen protecting group, under the conditions of process step (c) Amide bond formation as described herein.

Suitable nitrogen protecting groups are well described in the art and for example can be found in references such as Greene T. W., Wuts, P. G. M. Protective Groups in Organic Synthesis, Wiley-Interscience and Kocienski, P. J. Protecting Groups, Thieme.

Compounds of formula (XVIII) may be prepared by reacting compounds of formula (XVII), under the conditions of process step (e) Removal of a nitrogen protecting group.

The conditions required for removal of the protecting group are often specific to that protecting group; conditions for their removal may be found in references such as Greene T. W., Wuts, P. G. M. Protective Groups in Organic Synthesis, Wiley-Interscience and Kocienski, P. J. Protecting Groups, Thieme. If P is BOC, deprotection is acid catalysed removal of protecting group using a suitable solvent at room temperature Typically—the protected amine is treated with an excess of an acid such as HCl or TFA at room temperature in a solvent such as 1,4-dioxane, ethyl acetate, DCM or THF.

Preferably—the amine in dichloromethane was treated with 4N HCl in 1,4-dioxane and stirred at room temp for 18 hours.

Compounds of formula (XIX) may be prepared by reacting compounds of formula (IX) and (XVIII), under the conditions of process step (d) Reductive amination as described herein.

Compounds of formula (I) may be prepared by reacting compounds of formula (II) and (XIX), under the conditions of process step (c) Amide bond formation as described herein Compounds of formula (I) where $R^1$, $R^2$, $R^3$, $R^4$, z and y are as described above, x is 1 and $R^5$ is $C_{1-6}$ alkyl may be prepared by the following process as described in Scheme 6:

Scheme 6

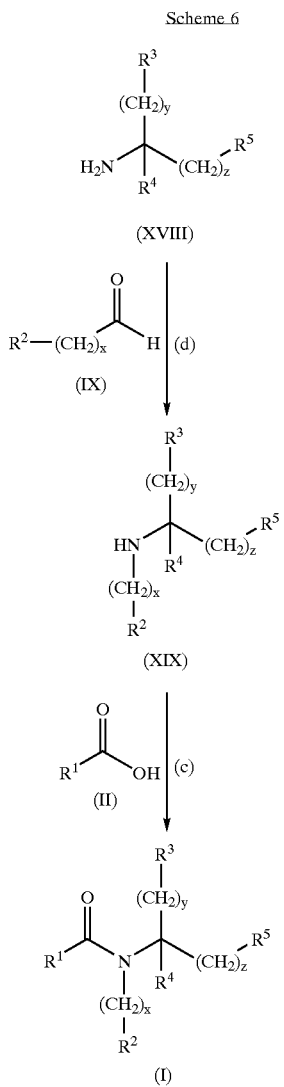

Compounds of formula (XIX) may be prepared by reacting compounds of formula (XVIII) and (IX), under the conditions of process step (d) Reductive amination as described herein.

Compounds of formula (I) may be prepared by reacting compounds of formula (XIX) and (II), under the conditions of process step (c) Amide bond formation as described herein.

Compounds of formula (I), wherein $R^1$ is phenyl or Aromatic Heterocycle, comprising an $SO_2Me$ substituent may be prepared by oxidation of the corresponding compound of formula (I) comprising an SMe substituent. Typically, the oxidation is carried out by addition of an oxidant to the sulfide in a solvent at ambient temperature. Preferably, the solvent is dichloromethane and the oxidant is 3-chloroperoxybenzoic acid.

Compounds of formula (I), wherein $R^1$ is phenyl or Aromatic Heterocycle, comprising an $NR^7R^8$ substituent may be prepared by reaction of the corresponding compound of formula (I) comprising an $SO_2Me$ substituent with an amine, $HNR^7R^8$. Typically, the reaction is carried out by addition of the amine to the sulfone in an organic solvent at a temperature of 0° C., followed by warming to room temperature for 2 hours. Preferably, the solvent is THF.

The compounds of the invention are useful because they have pharmacological activity in mammals, including humans. More particularly, they are useful in the treatment or prevention of a disorder in which elevated levels of oxytocin or an excessive response to a normal level of oxytocin are implicated. Disease states that may be mentioned include sexual dysfunction, particularly premature ejaculation, preterm labour, complications in labour, appetite and feeding disorders, obesity, benign prostatic hyperplasia, premature birth, dysmenorrhoea, congestive heart failure, arterial hypertension, liver cirrhosis, nephrotic hypertension, ocular hypertension, obsessive compulsive disorder and neuropsychiatric disorders.

Sexual dysfunction (SD) is a significant clinical problem which can affect both males and females. The causes of SD may be both organic as well as psychological. Organic aspects of SD are typically caused by underlying vascular diseases, such as those associated with hypertension or diabetes mellitus, by prescription medication and/or by psychiatric disease such as depression. Physiological factors include fear, performance anxiety and interpersonal conflict. SD impairs sexual performance, diminishes self-esteem and disrupts personal relationships thereby inducing personal distress. In the clinic, SD disorders have been divided into female sexual dysfunction (FSD) disorders and male sexual dysfunction (MSD) disorders (Melman et al 1999 J. Urology 161 5–11). FSD is best defined as the difficulty or inability of a woman to find satisfaction in sexual expression. Male sexual dysfunction (MSD) is generally associated with either erectile dysfunction, also known as male erectile dysfunction (MED) and/or ejaculatory disorders such as premature ejaculation, anorgasmia (unable to achieve orgasm) or desire disorders such as hypoactive sexual desire disorder (lack of interest in sex).

PE is a relatively common sexual dysfunction in men. It has been defined in several different ways but the most widely accepted is the Diagnostic and Statistical Manual of Mental Disorders IV one which states:

"PE is a lifelong persistent or recurrent ejaculation with minimal sexual stimulation before, upon or shortly after penetration and before the patient wishes it. The clinician must take into account factors that affect duration of the excitement phase, such as age, novelty of the sexual partner or stimulation, and frequency of sexual activity. The disturbance causes marked distress of interpersonal difficulty."

The International Classification of Diseases 10 definition states:

"There is an inability to delay ejaculation sufficiently to enjoy lovemaking, manifest as either of the following: (1) occurrence of ejaculation before or very soon after the beginning of intercourse (if a time limit is required: before or within 15 seconds of the beginning of intercourse); (2) ejaculation occurs in the absence of sufficient erection to make intercourse possible. The problem is not the result of prolonged abstinence from sexual activity"

Other definitions which have been used include classification on the following criteria:
Related to partner's orgasm
Duration between penetration and ejaculation
Number of thrust and capacity for voluntary control Psychological factors may be involved in PE, with relationship problems, anxiety, depression, prior sexual failure all playing a role.

Ejaculation is dependent on the sympathetic and parasympathetic nervous systems. Efferent impulses via the sympathetic nervous system to the vas deferens and the epididymis produce smooth muscle contraction, moving sperm into the posterior urethra. Similar contractions of the seminal vesicles, prostatic glands and the bulbouretheral glands increase the volume and fluid content of semen. Expulsion of semen is mediated by efferent impulses originating from the nucleus of Onuf in the spinal cord, which pass via the parasympathetic nervous system and cause rhythmic contractions of the bulbocavernous, ischiocavernous and pelvic floor muscles. Cortical control of ejaculation is still under debate in humans. In the rat the medial pre-optic area and the paraventricular nucleus of the hypothalamus seem to be involved in ejaculation.

Ejaculation comprises two separate components—emission and ejaculation. Emission is the deposition of seminal fluid and sperm from the distal epididymis, vas deferens, seminal vesicles and prostrate into the prostatic urethra. Subsequent to this deposition is the forcible expulsion of the seminal contents from the urethral meatus. Ejaculation is distinct from orgasm, which is purely a cerebral event. Often the two processes are coincidental.

A pulse of oxytocin in peripheral serum accompanies ejaculation in mammals. In man oxytocin but not vasopressin plasma concentrations are significantly raised at or around ejaculation. Oxytocin does not induce ejaculation itself; this process is 100% under nervous control via α1-adrenoceptor/sympathetic nerves originating from the lumbar region of the spinal cord. The systemic pulse of oxytocin may have a direct role in the peripheral ejaculatory response. It could serve to modulate the contraction of ducts and glandular lobules throughout the male genital tract, thus influencing the fluid volume of different ejaculate components for example. Oxytocin released centrally into the brain could influence sexual behaviour, subjective appreciation of arousal (orgasm) and latency to subsequent ejaculation.

Accordingly, one aspect of the invention provides for the use of a compound of formula (I) in the preparation of a medicament for the prevention or treatment of sexual dysfunction, preferably male sexual dysfunction, most preferably premature ejaculation.

It has been demonstrated in the scientific literature that the number of oxytocin receptors in a womans body increases during pregnancy, most markedly before the onset of labour. Without being bound by any theory it is known that the inhibition of oxytocin can assist in preventing preterm labour and in resolving complications in labour.

Accordingly, another aspect of the invention provides for the use of a compound of formula (I) in the preparation of a medicament for the prevention or treatment of preterm labour and complications in labour.

Oxytocin has a role in feeding; it stimulates a desire to eat. By inhibiting oxytocin it is possible to reduce the desire to eat. Accordingly oxytocin inhibitors are useful in treating appetite and feeding disorders. Further by reducing appetite, oxytocin inhibitors can help to treat obesity.

Accordingly, a further aspect of the invention provides for the use of a compound of formula (I) in the preparation of a medicament for the prevention or treatment of obesity, appetite and feeding disorders.

Oxytocin is implicated as one of the causes of benign prostatic hyperplasia (BPH). Analysis of prostate tissue have shown that patients with BPH have increased levels of oxytocin. Oxytocin antagonists can help treat this condition.

Accordingly, another aspect of the invention provides for the use of a compound of formula (I) in the preparation of a medicament for the prevention or treatment of benign prostatic hyperplasia.

It is to be appreciated that all references herein to treatment include curative, palliative and prophylactic treatment.

The compounds of the present invention may be coadministered with one or more agents selected from:
1) One or more SSRIs such as paroxetine, 3-[(dimethylamino)methyl]-4-[4-(methylsulfanyl) phenoxy]benzenesulfonamide (Example 28, WO 0172687), 3-[(dimethylamino)methyl]-4-[3-methyl-4-(methylsulfanyl)phenoxy]benzenesulfonamide (Example 12, WO 0218333), N-methyl-N-({3-[3-methyl-4-(methylsulfanyl)phenoxy]-4-pyridinyl}methyl)amine (Example 38, PCT Application no PCT/IB02/01032).
2) One or more local anaesthetics;
3) One or more beta adrenoceptor agonists;
4) one or more α-adrenergic receptor antagonists (also known as α-adrenoceptor blockers, α-receptor blockers or α-blockers); suitable α$_1$-adrenergic receptor antagonists include: phentolamine, prazosin, phentolamine mesylate, trazodone, alfuzosin, indoramin, naftopidil, tamsulosin, phenoxybenzamine, rauwolfa alkaloids, Recordati 15/2739, SNAP 1069, SNAP 5089, RS17053, SL 89.0591, doxazosin, Example 19 of WO9830560, terazosin and abanoquil; suitable α$_2$-adrenergic receptor antagonists include dibenamine, tolazoline, trimazosin, efaroxan, yohimbine, idazoxan clonidine and dibenamine; suitable non-selective α-adrenergic receptor antagonists include dapiprazole; further α-adrenergic receptor antagonists are described in PCT application WO99/30697 published on 14 Jun. 1998 and U.S. Pat. Nos. 4,188,390; 4,026,894; 3,511,836; 4,315,007; 3,527,761; 3,997,666; 2,503,059; 4,703,063; 3,381,009; 4,252,721 and 2,599,000 each of which is incorporated herein by reference;
5) one or more cholesterol lowering agents such as statins (e.g. atorvastatin/Lipitor-trade mark) and fibrates;
6) one or more of vasoactive intestinal protein (VIP), VIP mimetic, VIP analogue, more particularly mediated by one or more of the VIP receptor subtypes VPAC1, VPAC or PACAP (pituitary adenylate cyclase activating peptide), one or more of a VIP receptor agonist or a VIP analogue (eg Ro-125-1553) or a VIP fragment, one or more of a α-adrenoceptor antagonist with VIP combination eg Invicorp, Aviptadil);
7) one or more of a serotonin receptor agonist, antagonist or modulator, more particularly agonists, antagonists or modulators for example 5HT1A (including VML 670), 5HT2A, 5HT2C, 5HT3, 5HT6 and/or 5HT7 receptors, including those described in WO-09902159, WO-00002550 and/or WO-00028993;
8) one or more NEP inhibitors, preferably wherein said NEP is EC 3.4.24.11 and more preferably wherein said NEP inhibitor is a selective inhibitor for EC 3.4.24.11, more preferably a selective NEP inhibitor is a selective inhibitor for EC 3.4.24.11, which has an IC$_{5-0}$ of less than 100 nM (e.g. ompatrilat, sampatrilat) suitable NEP inhibitor compounds are described in EP-A-1097719; IC50 values against NEP and ACE may be determined using methods described in published patent application EP1097719-A1, paragraphs [0368] to [0376];
9) one or more of an agonist or modulator for vasopressin receptors, such as relcoraptan (SR 49059)
10) Apomorphine—teachings on the use of apomorphine as a pharmaceutical may be found in U.S. Pat. No. 5,945,117;
11) Dopamine D2 agonists (e.g. Premiprixal, Pharmacia Upjohn compound number PNU95666);
12) Melanocortin receptor agonists (e.g. Melanotan II);
13) PGE1 receptor agonists (e.g. alprostadil);
14) Mono amine transport inhibitors, particularly Noradrenaline Re-uptake Inhibitors (NRIs) (e.g. Reboxetine), other Serotonin Re-uptake Inhibitors (SRIs) (e.g. paroxetine) or Dopamine Re-uptake Inhibitors (DRIs);
15) 5-HT$_{1A}$ antagonists (e.g. robalzotan); and
16) PDE inhibitors such as PDE2 (e.g. erythro-9-(2-hydroxyl-3-nonyl)-adenine) and Example 100 of EP 0771799-incorporated herein by reference) and in particular a PDE5 inhibitor such as the pyrazolo[4,3-d]pyrimidin-7-ones disclosed in EP-A-0463756; the pyrazolo[4,3-d]pyrimidin-7-ones disclosed in EP-A-0526004; the pyrazolo[4,3-d]pyrimidin-7-ones disclosed in published international patent application WO 93/06104; the isomeric pyrazolo[3,4-d]pyrimidin-4-ones disclosed in published international patent application WO 93/07149; the quinazolin-4-ones disclosed in published international patent application WO 93/12095; the pyrido[3,2-d]pyrimidin-4-ones disclosed in published international patent application WO 94/05661; the purin-6-ones disclosed in published international patent application WO 94/00453; the pyrazolo[4,3-d]pyrimidin-7-ones disclosed in published international patent application WO 98/49166; the pyrazolo[4,3-d]pyrimidin-7-ones disclosed in published international patent application WO 99/54333; the pyrazolo[4,3-d]pyrimidin-4-ones disclosed in EP-A-0995751; the pyrazolo[4,3-d]pyrimidin-7-ones disclosed in published international patent application WO 00/24745; the pyrazolo[4,3-d]pyrimidin-4-ones disclosed in EP-A-0995750; the compounds disclosed in published international application WO95/19978; the compounds disclosed in published international application WO 99/24433 and the compounds disclosed in published international application WO 93/07124.

The pyrazolo[4,3-d]pyrimidin-7-ones disclosed in published international application WO 01/27112; the pyrazolo[4,3-d]pyrimidin-7-ones disclosed in published international application WO 01/27113; the compounds disclosed in EP-A-1092718 and the compounds disclosed in EP-A-1092719.

Preferred PDE5 inhibitors for use with the invention:
5-[2-ethoxy-5-(4-methyl-1-piperazinylsulphonyl)phenyl]-1-methyl-3-n-propyl-1,6-dihydro-7H-pyrazolo[4,3-d]pyrimidin-7-one (sildenafil) also known as 1-[[3-(6,7-dihydro-1-methyl-7-oxo-3-propyl-1H-pyrazolo[4,3-d]pyrimidin-5-yl)-4-ethoxyphenyl]sulphonyl]-4-methylpiperazine (see EP-A-0463756);
5-(2-ethoxy-5-morpholinoacetylphenyl)-1-methyl-3-n-propyl-1,6-dihydro-7H-pyrazolo[4,3-d]pyrimidin-7-one (see EP-A-0526004);
3-ethyl-5-[5-(4-ethylpiperazin-1-ylsulphonyl)-2-n-propoxyphenyl]-2-(pyridin-2-yl)methyl-2,6-dihydro-7H-pyrazolo[4,3-d]pyrimidin-7-one (see WO98/49166);
3-ethyl-5-[5-(4-ethylpiperazin-1-ylsulphonyl)-2-(2-methoxyethoxy)pyridin-3-yl]-2-(pyridin-2-yl)methyl-2,6-dihydro-7H-pyrazolo[4,3-d]pyrimidin-7-one (see WO99/54333);

(+)-3-ethyl-5-[5-(4-ethylpiperazin-1-ylsulphonyl)-2-(2-methoxy-1 (R)-methylethoxy)pyridin-3-yl]-2-methyl-2,6-dihydro-7H-pyrazolo[4,3-d]pyrimidin-7-one, also known as 3-ethyl-5-(5-[4-ethylpiperazin-1-ylsulphonyl]-2-([(1R)-2-methoxy-1-methylethyl]oxy)pyridin-3-yl)-2-methyl-2,6-dihydro-7H-pyrazolo[4,3-d]pyrimidin-7-one (see WO99/54333);
5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one, also known as 1-{6-ethoxy-5-[3-ethyl-6,7-dihydro-2-(2-methoxyethyl)-7-oxo-2H-pyrazolo[4,3-d]pyrimidin-5-yl]-3-pyridylsulphonyl}-4-ethylpiperazine (see WO 01/27113, Example 8);
5-[2-iso-Butoxy-5-(4-ethylpiperazin-1-ylsulphonyl)pyridin-3-yl]-3-ethyl-2-(1-methylpiperidin-4-yl)-2,6-dihydro-7H-pyrazolo[4,3-d]pyrimidin-7-one (see WO 01/27113, Example 15);
5-[2-Ethoxy-5-(4-ethylpiperazin-1-ylsulphonyl)pyridin-3-yl]-3-ethyl-2-phenyl-2,6-dihydro-7H-pyrazolo[4,3-d]pyrimidin-7-one (see WO 01/27113, Example 66);
5-(5-Acetyl-2-propoxy-3-pyridinyl)-3-ethyl-2-(1-isopropyl-3-azetidinyl)-2,6-dihydro-7H-pyrazolo[4,3-d]pyrimidin-7-one (see WO 01/27112, Example 124);
5-(5-Acetyl-2-butoxy-3-pyridinyl)-3-ethyl-2-(1-ethyl-3-azetidinyl)-2,6-dihydro-7H-pyrazolo[4,3-d]pyrimidin-7-one (see WO 01/27112, Example 132);
(6R,12aR)-2,3,6,7,12,12a-hexahydro-2-methyl-6-(3,4-methylenedioxyphenyl)-pyrazino[2',1':6,1]pyrido[3,4-b]indole-1,4-dione (IC-351), i.e. the compound of examples 78 and 95 of published international application WO95/19978, as well as the compound of examples 1, 3, 7 and 8;
2-[2-ethoxy-5-(4-ethyl-piperazin-1-yl-1-sulphonyl)-phenyl]-5-methyl-7-propyl-3H-imidazo[5,1-f][1,2,4]triazin-4-one (vardenafil) also known as 1-[[3-(3,4-dihydro-5-methyl-4-oxo-7-propylimidazo[5,1-f]-as-triazin-2-yl)-4-ethoxyphenyl]sulphonyl]-4-ethylpiperazine, i.e. the compound of examples 20, 19, 337 and 336 of published international application WO99/24433; and
the compound of example 11 of published international application WO93/07124 (EISAI); and
compounds 3 and 14 from Rotella D P, J. Med. Chem., 2000, 43, 1257.

Still further PDE5 inhibitors for use with the invention include: 4-bromo-5-(pyridylmethylamino)-6-[3-(4-chlorophenyl)-propoxy]-3(2H)pyridazinone; 1-[4-[(1,3-benzodioxol-5-ylmethyl)amiono]-6-chloro-2-quinozolinyl]-4-piperidine-carboxylic acid, monosodium salt; (+)-cis-5,6a,7,9,9,9a-hexahydro-2-[4-(trifluoromethyl)-phenylmethyl-5-methyl-cyclopent-4,5]imidazo[2,1-b]purin-4(3H)one; furazlocillin; cis-2-hexyl-5-methyl-3,4,5,6a,7,8,9,9a-octahydrocyclopent[4,5]-imidazo[2,1-b]purin-4-one; 3-acetyl-1-(2-chlorobenzyl)-2-propylindole-6-carboxylate; 3-acetyl-1-(2-chlorobenzyl)-2-propylindole-6-carboxylate; 4-bromo-5-(3-pyridylmethylamino)-6-(3-(4-chlorophenyl)propoxy)-3-(2H)pyridazinone; 1-methyl-5(5-morpholinoacetyl-2-n-propoxyphenyl)-3-n-propyl-1,6-dihydro-7H-pyrazolo(4,3-d)pyrimidin-7-one; 1-[4-[(1,3-benzodioxol-5-ylmethyl)amino]-6-chloro-2-quinazolinyl]-4-piperidinecarboxylic acid, monosodium salt; Pharmaprojects No. 4516 (Glaxo Wellcome); Pharmaprojects No. 5051 (Bayer); Pharmaprojects No. 5064 (Kyowa Hakko; see WO 96/26940); Pharmaprojects No. 5069 (Schering Plough); GF-196960 (Glaxo Welcome); E-8010 and E-4010 (Eisai); Bay-38-3045 & 38-9456 (Bayer) and Sch-51866.

The contents of the published patent applications and journal articles and in particular the general formulae of the therapeutically active compounds of the claims and exemplified compounds therein are incorporated herein in their entirety by reference thereto.

More preferred PDE5 inhibitors for use with the invention are selected from the group:

5-[2-ethoxy-5-(4-methyl-1-piperazinylsulphonyl)phenyl]-1-methyl-3-n-propyl-1,6-dihydro-7H-pyrazolo[4,3-d]pyrimidin-7-one (sildenafil);

(6R, 12aR)-2,3,6,7,12,12a-hexahydro-2-methyl-6-(3,4-methylenedioxyphenyl)-pyrazino[2', 1':6,1]pyrido[3,4-b]indole-1,4-dione (IC-351);

2-[2-ethoxy-5-(4-ethyl-piperazin-1-yl-1-sulphonyl)-phenyl]-5-methyl-7-propyl-3H-imidazo[5,1-f][1,2,4]triazin-4-one (vardenafil); and 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one or 5-(5-Acetyl-2-butoxy-3-pyridinyl)-3-ethyl-2-(1-ethyl-3-azetidinyl)-2,6-dihydro-7H-pyrazolo[4,3-d]pyrimidin-7-one and pharmaceutically acceptable salts thereof.

A particularly preferred PDE5 inhibitor is 5-[2-ethoxy-5-(4-methyl-1-piperazinylsulphonyl)phenyl]-1-methyl-3-n-propyl-1,6-dihydro-7H-pyrazolo[4,3-d]pyrimidin-7-one (sildenafil) (also known as 1-[[3-(6,7-dihydro-1-methyl-7-oxo-3-propyl-1H-pyrazolo[4,3-d]pyrimidin-5-yl)-4-ethoxyphenyl]sulphonyl]-4-methylpiperazine) and pharmaceutically acceptable salts thereof. Sildenafil citrate is a preferred salt.

The compounds of the formula (I) can also be administered together with

A. Oxytocin Receptor Ligand Binding IC50 Assay
i) Buffers

| Cell Growth Medium | Hams F12 Nutrient Mix<br>10% FCS<br>2 mM L-Glutamine<br>400 µg/ml G418<br>15 mM HEPES |
|---|---|
| Membrane Prep Buffer | 50 mM Tris-HCl, pH 7.8<br>10 mM MgCl$_2$<br>Protease Inhibitors |
| Freezing Buffer | 50 mM Tris-HCl, pH 7.8<br>10 mM MgCl$_2$<br>20% Glycerol |
| Assay Medium | 50 mM Tris-HCl, pH 7.8<br>10 mM MgCl$_2$<br>0.25% BSA |
| Max. | 0.5 µM (arg$^8$)-vasotocin made in 2.5% DMSO/50 mM Tris-HCL, pH 7.8, 10 mM MgCl$_2$ |
| Min. | 2.5% DMSO/50 mM Tris-HCL, pH 7.8, 10 mM MgCl$_2$ | ii) Compound Dilution (Final concentration of 10 µM in the assay)
a) HTA stock compounds at 4 mM in 100% DMSO
b) Dilute compounds to 200 µM in dH$_2$O.
c) Further dilute compounds to 100 µM in 100 mM Tris-HCl, pH 7.8, 20 mM MgCl$_2$. This gives final concentrations of 2.5% DMSO, 50 mM Tris-HCl, pH 7.8, 10 mM MgCl$_2$.
d) Using the diluted stock, prepare 1:2 dilutions over 10 points in 50 mM Tris-HCl, pH 7.8, 10 mM MgCl$_2$, 2.5% DMSO with the TECAN Genesis.
e) Dispense 10 µl of the compound into a 384 well Optiplate according to the plate layout required for analysis by ECADA leaving space for the standard (arg$^8$)-vasotocin IC50. These plates can be stored at 4° C.
f) On the day of the assay, add 10 µl of Max. to the + wells and 10 µl of Min. to the − wells, and a 1:2 serial dilution over 10 points in duplicate of the (arg$^8$)-vasotocin with a top concentration of 100 nM (20 nM final).

iii) Maintenance of the Oxytocin Receptor —CHO Cells

The cell line is routinely maintained as a continuous culture in 50 ml growth medium in 225 cm$^2$ flasks.

Cells are passaged by removing the medium from the monolayer, washing with PBS and incubating with Trypsin until cells show signs of dissociation. After knocking the cells from the bottom of the flask, cells are resuspended in growth medium and seeded into 225 cm$^2$ flasks at a concentration of 8×10$^5$ cells/flask.

IV) Growth of Cells in Roller Bottles

Cells are seeded into 10×850 cm$^2$ roller bottles at a density of 6×10$^6$ cells/bottle and are allowed to reach near confluence.

Cells are removed from the bottles using trypsin, as described above, and the cells are seeded into 100× roller bottles (i.e. 1:10 split ratio).

Cells are again allowed to reach near confluence before removing the growth medium, adding 40 ml PBS/bottle and harvesting by scraping using the CellMate. The cell suspension is then centrifuged at 2000 rpm, washed in PBS, centrifuged again and pellets are frozen in aliquots at −80° C.

V) Membrane Preparations

Cell pellets are retrieved from the freezer, thawed on ice and resuspended in 3 ml of membrane prep buffer per ml packed cell volume.

The suspension is then homogenised using a mechanical homogeniser for several bursts of 5 secs on ice before centrifuging at 25,000×g for 30 mins.

After resuspending the pellet in 1 ml of freezing buffer per 1 ml of the original packed cell volume the suspension is briefly homogenised to remove small lumps. Protein concentrations are then measured and the membrane suspension is finally frozen in aliquots at a minimum of 5 mg/ml at −80° C.

vi) Assay

Membranes are thawed on ice before diluting to 1 mg/ml in assay buffer. SPA beads are resuspended at 50 mg/ml in assay buffer. From these concentrations, beads are pre-coupled with membranes by incubating 30 µg of protein per mg of bead on a top-to-tail shaker for 2 hours at 4° C. The bead/membranes are then centrifuged at 2000 rpm for 10 mins and the pellet is resuspended at 3 mg/ml.

All manipulations of the $^{125}$I-OVTA are carried out using tips that have been silanised using SigmaCote. All bottles and tubes are also silanised. The $^{125}$I-OVTA is diluted in 1 ml assay buffer per 50 µCi of lyophilised ligand. A 5 µl sample is then counted in duplicate using liquid scintillation counting (protocol 61 on Wallac Counter) and the concentration of the ligand is calculated (see example below). This is to overcome any loss of ligand due to stickiness. Using the measured concentration, the $^{125}$I-OVTA is diluted to 0.3 nM in assay buffer.

Example:

If 5 µl gives 500000 dpm and the specific activity of the ligand is 2200 Ci/mmol then:

Concentration=500000/(2.2×2200×5) nM

20 µl of the bead/membrane preparation is added to the prepared Optiplates using the Multi-drop. The bead/membrane preparation is kept in suspension using a stirring flask. 20 µl of the $^{125}$I-OVTA is then added to each well of the Optiplate using the Multi-drop. Following a 4 hour incubation at room temperature, the plates are counted using the TopCount NXT for 30 s/well.

The compounds of the present invention all exhibit better than 70% inhibition of oxytocin at 100M.

2-Amino-N-[carbamoyl-(2,3-dihydro-benzo[1,4]dioxin-6-yl)-methyl]-4,6-dimethyl-N-(4-methyl-benzyl)-nicotinamide (Example 257) has a $K_i$ of 9.4 nM (R or S)-2-Amino-N-[carbamoyl-{(3-methoxyphenyl)-methyl}]-4,6-dimethyl-N-(4-methyl-benzyl)-nicotinamide (Example 258-single enantiomer) has a $K_i$ of 9.4 nM The compounds of the formula (I) can be administered alone but will generally be administered in admixture with a suitable pharmaceutical excipient, diluent or carrier selected with regard to the intended route of administration and standard pharmaceutical practice.

The present invention provides for a composition comprising a compound of formula (i) and a pharmaceutically acceptable diluent or carrier.

For example, the compounds of the formula (I) can be administered orally, buccally or sublingually in the form of tablets, capsules, ovules, elixirs, solutions or suspensions, which may contain flavouring or colouring agents, for immediate-, delayed-, modified-, sustained-, pulsed- or controlled-release applications.

Such tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the compounds of the formula (I) may be combined with various sweetening or flavouring agents, colouring matter or dyes, with emulsifying and/or suspending agents and with diluents such as water, ethanol, propylene glycol and glycerin, and combinations thereof.

The compounds of the formula (I) can also be administered parenterally, for example, intravenously, intra-arterially, intraperitoneally, intrathecally, intraventricularly, intraurethrally, intrasternally, intracranially, intramuscularly or subcutaneously, or they may be administered by infusion techniques. For such parenteral administration they are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

The compounds of formula (I) can also be administered intranasally or by inhalation and are conveniently delivered in the form of a dry powder inhaler or an aerosol spray presentation from a pressurised container, pump, spray, atomiser or nebuliser, with or without the use of a suitable propellant, e.g. dichlorodifluoromethane, trichlorofluoromethane, dichlorotetrafluoroethane, a hydrofluoroalkane such as 1,1,1,2-tetrafluoroethane (HFA 134A [trade mark]) or 1,1,1,2,3,3,3-heptafluoropropane (HFA 227EA [trade mark]), carbon dioxide or other suitable gas. In the case of a pressurised aerosol, the dosage unit may be determined by providing a valve to deliver a metered amount. The pressurised container, pump, spray, atomiser or nebuliser may contain a solution or suspension of the active compound, e.g. using a mixture of ethanol and the propellant as the solvent, which may additionally contain a lubricant, e.g. sorbitan trioleate.

Capsules and cartridges (made, for example, from gelatin) for use in an inhaler or insufflator may be formulated to contain a powder mix of a compound of the formula (I) and a suitable powder base such as lactose or starch.

Alternatively, the compounds of the formula (I) can be administered in the form of a suppository or pessary, or they may be applied topically in the form of a gel, hydrogel, lotion, solution, cream, ointment or dusting powder. The compounds of the formula (I) may also be dermally or transdermally administered, for example, by the use of a skin patch. They may also be administered by the pulmonary or rectal routes.

They may also be administered by the ocular route. For ophthalmic use, the compounds can be formulated as micronised suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For application topically to the skin, the compounds of the formula (I) can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

The compounds of the formula (I) may also be used in combination with a cyclodextrin. Cyclodextrins are known to form inclusion and non-inclusion complexes with drug molecules. Formation of a drug-cyclodextrin complex may modify the solubility, dissolution rate, bioavailability and/or stability property of a drug molecule. Drug-cyclodextrin complexes are generally useful for most dosage forms and administration routes. As an alternative to direct complexation with the drug the cyclodextrin may be used as an auxiliary additive, e.g. as a carrier, diluent or solubiliser. Alpha-, beta- and gamma-cyclodextrins are most commonly used and suitable examples are described in WO-A-91/11172, WO-A-94/02518 and WO-A-98/55148.

The invention is further illustrated by the following, non-limiting examples.

| Abbreviations and Definitions: | |
|---|---|
| Arbocel ™ | Filtration agent, from J. Rettenmaier & Sohne, Germany |
| Amberlyst ® 15 | Ion exchange resin, available from Aldrich Chemical Company |
| APCI | Atmospheric Pressure Chemical Ionisation |
| atm | Pressure in atmospheres (1 atm = 760 Torr = 101.3 kPa) |
| Biotage ™ | Chromatography performed using Flash 75 silica gel cartridge, from Biotage, UK |
| BOC | tert-Butyloxycarbonyl group |
| br | Broad |
| c | Concentration used for optical rotation measurements in g per 100 ml (1 mg/ml is c 0.10) |
| cat | Catalytic |
| d | Doublet |
| dd | Doublet of doublets |
| Degussa ® 101 | 10 wt % palladium on activated carbon, Degussa type E101 available from Aldrich Chemical Company |
| Develosil Combi-RP $C_{30}$ hplc column | Supplied by Phenomenex - manufactured by Nomura Chemical Co. Composed of spherical silica particles (size 3 μm or 5 μm) which have a chemically bonded surface of C30 chains. These particles are packed into stainless steel columns of dimensions 2 cm internal diameter and 25 cm long. |
| Dowex ® | Ion exchange resin, from Aldrich Chemical Company |
| ee | Enantiomeric excess |
| HRMS | High Resolution Mass Spectrocopy (electrospray ionisation positive scan) |
| Hyflo ™ | Hyflo supercel ®, from Aldrich Chemical Company |
| liq | Liquid |
| LRMS | Low Resolution Mass Spectroscopy (electrospray or thermospray ionisation positive scan) |
| LRMS (ES⁻) | Low Resolution Mass Spectroscopy (electrospray ionisation negative scan) |
| m | Multiplet |
| m/z | Mass spectrum peak |
| MCI ™ gel | High porous polymer, CHP20P 75–150 □m, from Mitsubishi Chemical Corporation |
| Phenomenex Luna C18 hplc column | Supplied by Phenomenex. Composed of spherical silica particles (size 5 μm or 10 μm) which have a chemically bonded surface of C18 chains. These particles are packed into a stainless steel column of dimensions 2.1 cm internal diameter and 25 cm long. |
| psi | Pounds per square inch (1 psi = 6.9 kPa) |
| q | Quartet |
| $R_f$ | Retention factor on TLC |
| s | Singlet |
| Sep-Pak ® | Reverse phase $C_{18}$ silica gel cartridge, Waters Corporation |
| t | Triplet |
| TLC | Thin Layer Chromatography |
| □ | Chemical shift |

EXAMPLE 1

2-Amino-N-[2-amino-1-(2-methylphenyl)-2-oxoethyl]-N-(4-chlorobenzyl)nicotinamide

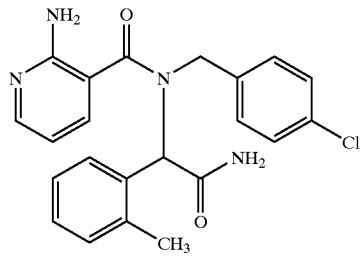

Solutions of 4-chlorobenzylamine (708 mg, 5 mmol) in methanol (10 ml), followed by o-tolualdehyde (601 mg, 5 mmol) in methanol (10 ml) then the compound from preparation 6 (916 mg, 5 mmol) in methanol/cyclohexane (95:5, by volume) were added consecutively to a suspension of 2-aminonicotinic acid (691 mg, 5 mmol) in methanol (20 ml), and the mixture stirred at 50° C. for 7 hours, then at room temperature for a further 18 hours. The reaction mixture was concentrated under reduced pressure, the residue dissolved in a solution of hydrochloric acid in tetrahydrofuran (25 ml, 0.6M) and the reaction stirred at room temperature for 24 hours. The mixture was evaporated under reduced pressure, the residue suspended in dichloromethane (200 ml), triethylamine added, until dissolution occurred, then the solution washed with saturated aqueous ammonium chloride solution (2×50 ml). The organic solution was then dried (MgSO₄) and evaporated under reduced pressure. The crude product was purified by column chromatography on silica gel using a gradient elution of dichloromethane:methanol:triethylamine (100:0:0 to 90:10:1) to afford the title compound, 968 mg.

¹Hnmr (CDCl₃, 400 MHz) □: 2.15 (s, 3H), 4.28 (d, 1H), 4.73 (d, 1H), 5.60 (m, 3H), 6.48–6.56 (m, 3H), 6.92–7.19 (m, 5H), 7.25 (s, 2H), 7.41 (m, 2H), 8.06 (d, 1H).

LRMS m/z (ES⁺) 409, 411 [MH⁺]

EXAMPLES 2 TO 218

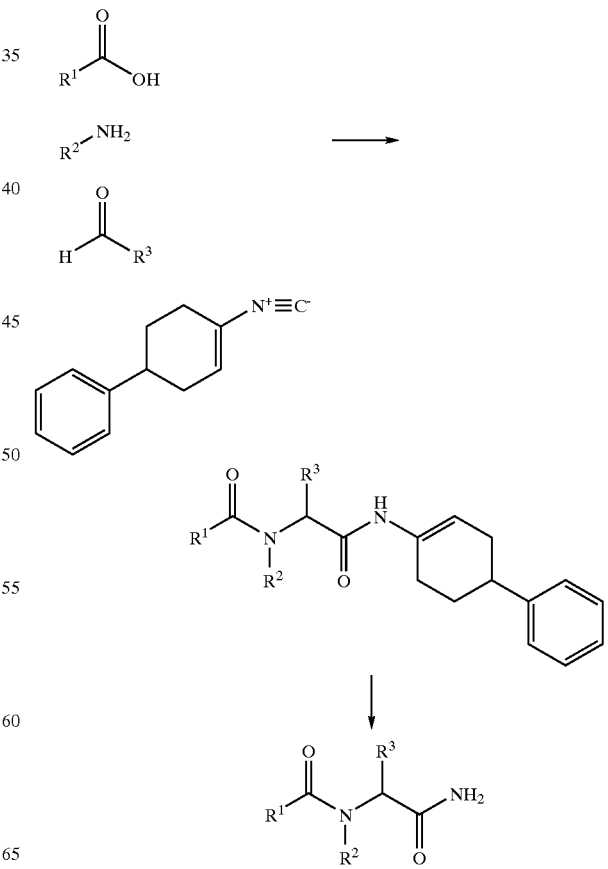

EXAMPLES 2 TO 8

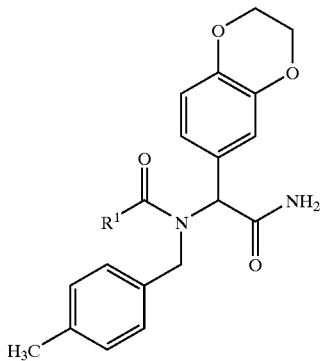

Solutions of 4-methylbenzylamine (50 µl, 0.6M in methanol), benzadioxane aldehyde (100 µl, 0.3M in methanol) and the isocyanate from preparation 6 (50 µl, 0.6M in methanol) were added to the appropriate acids (30 µmol). The reactions were sealed and agitated at rt for 18 hours then heated at 50° C. for 3 hours. The solvents were removed under reduced pressure, hydrochloric acid in tetrahydrofuran (500 µl, 0.6M) was added, and the vessels were resealed and agitated again at room temperature for a further 24 hours. The solvents were removed under reduced pressure, the residues dissolved in dimethyl sulphoxide (500 µl) and purified by HPLC, using a Phenomonex Luna 150×10 mm, 10 µm column, in acetonitile: 0.1% aqueous diethylamine, at 8 mlmin$^{-1}$, at 225 nM, using the following gradient.

| Time (min) | % acetonitrile |
|---|---|
| 0.00–0.50 | 5 |
| 0.50–0.60 | 5–20 |
| 0.60–6.50 | 20–95 |
| 6.5–8.5 | 95 |
| 8.5–8.6 | 95–5 |

| Ex. No. | R1 | Retention time/min |
|---|---|---|
| 2 | 2-CH3, 3-F phenyl | 6.163 |
| 3 | 2,4-diCH3 phenyl | 6.372 |
| 4 | 2-CH3, 4-CF3 phenyl | 6.355 |
| 5 | 2,6-diF phenyl | 5.883 |
| 6 | 2,3,4-triF phenyl | 6.267 |
| 7 | 2,4-diF phenyl | 5.988 |
| 8 | 2-CH3, 4-CH3 phenyl | 6.437 |

EXAMPLE 9

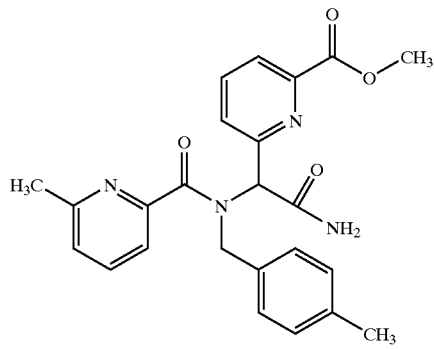

Example 9 was prepared from methyl(3-carboxaldehyde-2-pyridine)carboxylate, 4-methylbenzylamine, 6-methyl-2-pyridine carboxylic acid and the isocyanate from preparation 6, following a similar procedure to that described in example 2.

Retention time/min: 6.647

EXAMPLES 10 TO 24

The required acids (R$^1$CO$_2$H) (200 µl, 0.25M solution in methanol), (1-methyl-2-pyrrolidinone added to aid dissolution where necessary), followed by the amines (R$^2$NH$_2$) (100 µl, 0.5 M solution in methanol) were transferred to 96 well plates. Solutions of the appropriate aldehydes R$^3$COH (100 µl, 0.5 M solution in methanol) were prepared and then added, followed by a solution of the compound from preparation 6 (100 µl, 0.5M in cyclohexane:methanol, 1:19, by volume), and the plates sealed. The plates were heated at 50° C. for 24 hours under a nitrogen atmosphere, then allowed to cool and the solvents removed in vacuo.

A solution of hydrochloric acid in tetrahydrofuran (0.5 ml, 0.6N) was added and the reactions sealed and shaken at room temperature for 72 hours. The solvent was removed in vacuo, and the residues neutralised by the addition of triethylamine (50 µl), then dissolved in methyl sulphoxide/water (approx. 0.5 ml, 90:10, by volume). The solutions were purified by HPLC, on a Phenomenex Magellen 5µ C18 column (150×10 mm), using an elution gradient of acetonitrile: 0.05% aqueous trifluoroacetic acid (15:85 to 90:10 to 98:2) at 6 mlmin$^{-1}$ and detected at 210 nm, and the solvents evaporated in vacuo, to afford the title compounds.

The final compounds were analysed on a Phenomenex Magellen 5µ C18 column (30×4.6 mm), using acetonitile: 0.05% aqueous trifluoroacetic acid, at a rate of 3 mlmin$^{-1}$, at 225 nM and 255 nM, using the following gradient:

| Time (min) | % acetonitrile |
|---|---|
| 0.00–2.5 | 5–95 |
| 2.5–3.00 | 95 |
| 3.00–3.50 | 5 |

| Ex. No | R1 | R2 | R3 | RT/min |
|---|---|---|---|---|
| 18 | 4,6-dimethyl-3-yl-2-aminopyridine | 4-methylbenzyl | 3-methoxyphenyl | 1.28 |
| 19 | 4,6-dimethyl-3-yl-2-aminopyridine | 4-methylbenzyl | 4-methoxyphenyl | 1.28 |
| 20 | 4,6-dimethyl-3-yl-2-aminopyridine | 4-methylbenzyl | phenyl | 1.28 |
| 21 | 4,6-dimethyl-3-yl-2-aminopyridine | 4-methylbenzyl | 6-methylpyridin-2-yl | 1.18 |
| 22 | 4,6-dimethyl-3-yl-2-aminopyridine | 4-methylbenzyl | 2-methylphenyl | 1.39 |
| 23 | 4,6-dimethyl-3-yl-2-aminopyridine | 4-methylbenzyl | 3-methylphenyl | 1.38 |
| 24 | 4,6-dimethyl-3-yl-2-aminopyridine | 4-methylbenzyl | 4-chlorophenyl | 1.43 |

EXAMPLES 25 TO 62

The required acids ($R^1CO_2H$) (200 µl, 0.25M solution in 1-methyl-2-pyrrolidinone), followed by the amines ($R^2NH_2$) (100 µl, 0.5 M solution in methanol) were transferred to 96 well plates. Solutions of the appropriate aldehydes $R^3COH$ (100%, 0.5 M solution in methanol) were prepared and then added, followed by a solution of the compound from preparation 6 (100 µl, 0.5M in cyclohexane:methanol, 1:13, by volume), and the plates sealed. The plates were heated at 50° C. for 24 hours under a nitrogen atmosphere, then allowed to cool and the solvents removed in vacuo.

A solution of hydrochloric acid in tetrahydrofuran (0.5 ml, 0.6N) was added and the reactions sealed and shaken at room temperature for 24 hours. The solvent was removed in vacuo, and the residues dissolved in methyl sulphoxide/water (0.5 ml, 90:10, by volume). The solutions were purified by HPLC, on a Phenomenex Magellen 5µ C18 column (150×10 mm), using an elution gradient of acetonitrile: 0.05% aqueous trifluoroacetic acid (15:85 to 90:10 to 98:2) at 6 mlmin$^{-1}$ over 10 minutes and detected at 210 nm, and the solvents evaporated in vacuo, to afford the title compounds.

The final compounds were analysed on a Phenomenex Magellen 5µ C18 column (30×4.6 mm), using acetonitile: 0.05% aqueous trifluoroacetic acid, at a rate of 3 mlmin$^{-1}$, at 225 nM and 255 nM, using the following gradient:

| Time (min) | % acetonitrile |
|---|---|
| 0.00–2.5 | 5–95 |
| 2.5–3.00 | 95 |
| 3.00–3.50 | 5 |
| Ex. No | R1 | R2 | R3 | RT/min |
|---|---|---|---|---|
| 25 | 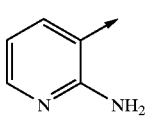 | 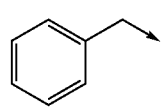 | 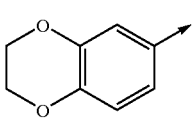 | 1.21 |
| 26 | 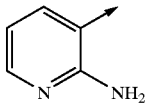 | 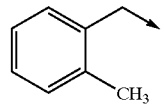 | 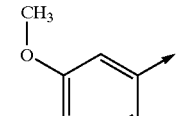 | 1.32 |
| 27 | 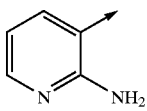 | 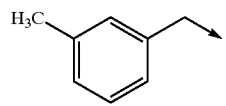 | 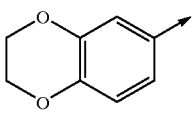 | 1.29 |
| 28 | 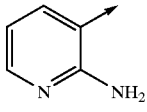 | 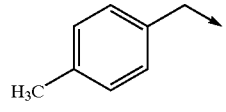 | 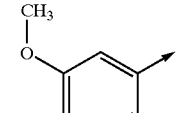 | 1.34 |
| 29 | 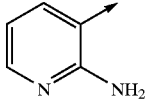 | 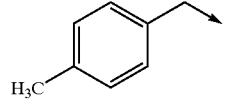 | 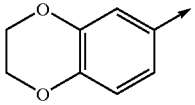 | 0.61 |
| 30 | 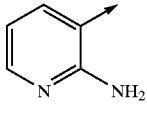 | 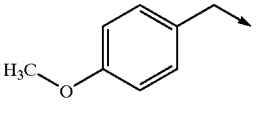 | 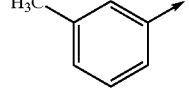 | 1.3 |
| 31 | 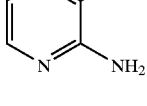 | 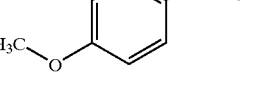 | 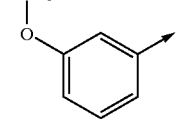 | 1.23 |
| 32 | 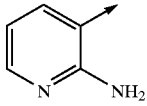 | 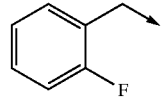 | 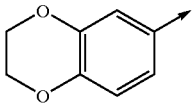 | 1.21 |
| 33 | 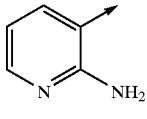 | 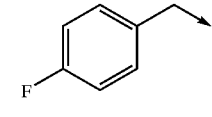 | 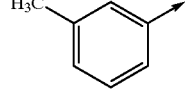 | 1.36 |

-continued
| Ex. No | R1 | R2 | R3 | RT/min |
|---|---|---|---|---|
| 34 | 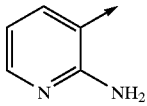 | 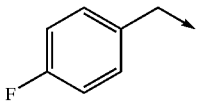 | 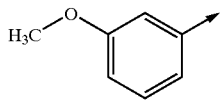 | 1.28 |
| 35 | 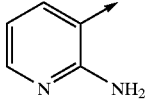 | 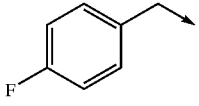 | 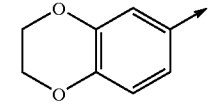 | 1.24 |
| 36 | 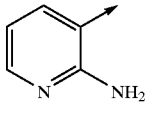 | 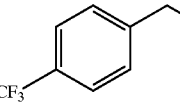 | 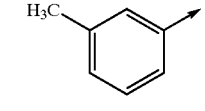 | 1.55 |
| 37 | 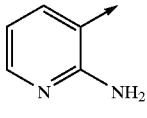 | 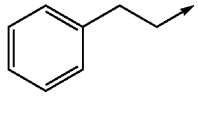 | 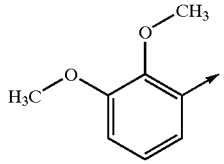 | 1.34 |
| 38a | 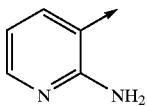 | 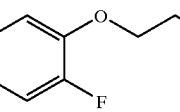 | 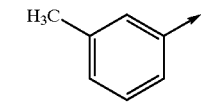 | 1.33 |
| 39 | 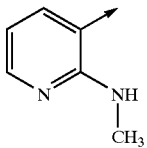 | 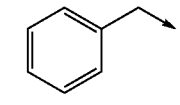 | 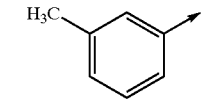 | 1.44 |
| 40 | 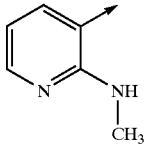 | 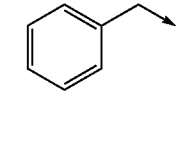 | 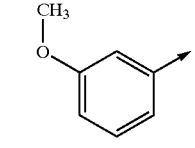 | 1.35 |
| 41 | 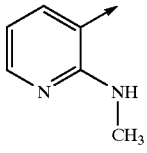 | 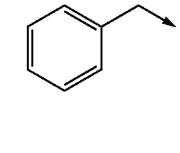 | 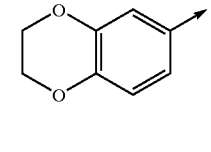 | 1.3 |
| 42 | 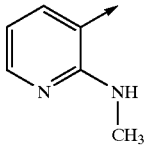 | 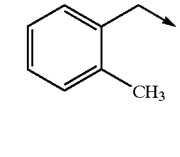 | 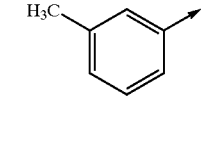 | 1.52 |
| 43 | 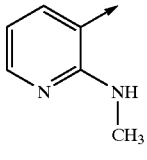 | 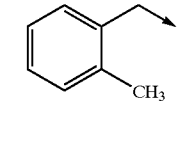 | 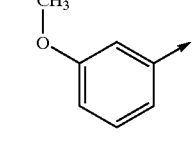 | 1.41 |

-continued
| Ex. No | R1 | R2 | R3 | RT/min |
|---|---|---|---|---|
| 44 |  | 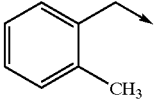 | 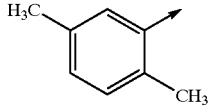 | 1.61 |
| 45 | 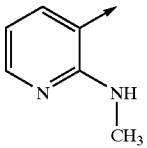 | 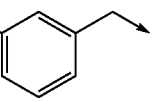 | 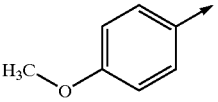 | 1.31 |
| 46 | 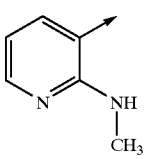 | 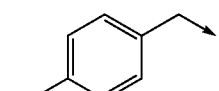 | 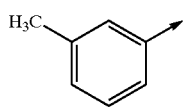 | 1.56 |
| 47 | 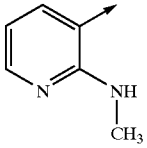 | 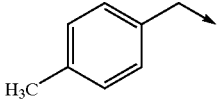 | 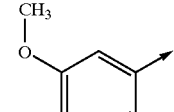 | 1.45 |
| 48 | 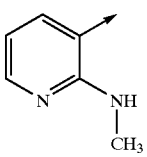 | 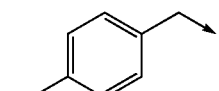 | 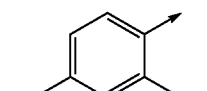 | 1.57 |
| 49 | 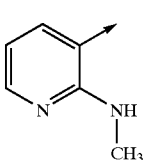 | 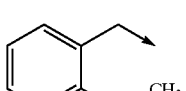 | 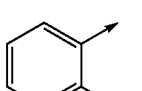 | 1.44 |
| 50 | 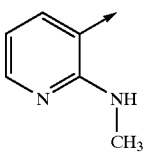 | 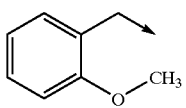 | 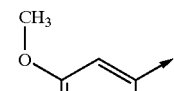 | 1.36 |
| 51 | 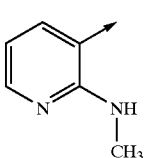 | 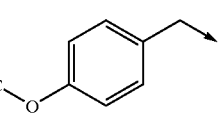 | 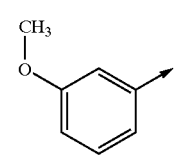 | 1.31 |
| 52 | 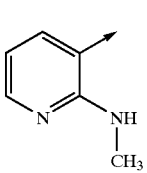 | 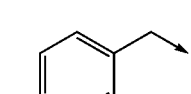 | 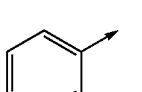 | 1.47 |

-continued
| Ex. No | R1 | R2 | R3 | RT/min |
|---|---|---|---|---|
| 53 | 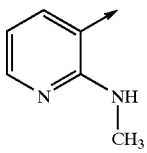 | 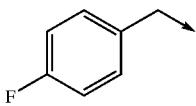 | 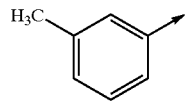 | 1.47 |
| 54 | 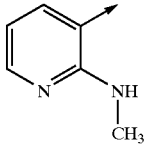 | 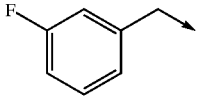 | 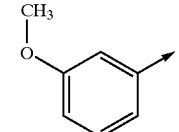 | 1.38 |
| 55 | 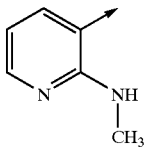 | 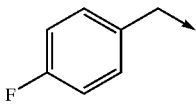 | 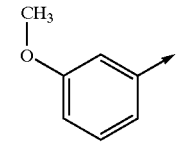 | 1.37 |
| 56 | 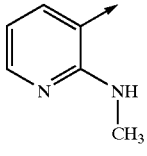 | 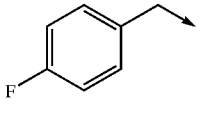 | 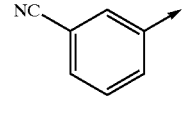 | 1.31 |
| 57 |  | 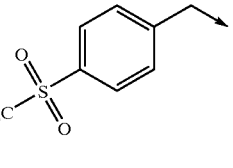 | 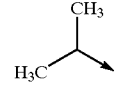 | 0.98 |
| 58 | 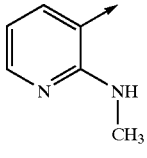 | 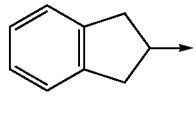 | 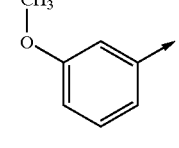 | 1.51 |
| 59b | 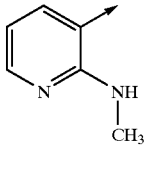 | 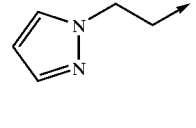 | 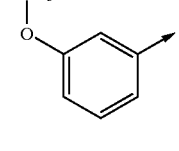 | 1.04 |
| 60 | 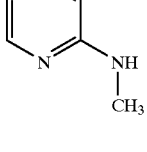 | 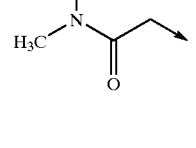 | 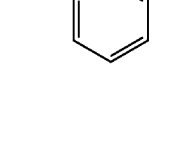 | 0.95 |
| 61 | 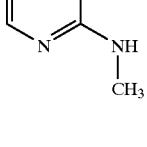 | 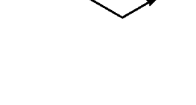 | 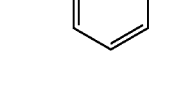 | 1.33 |

| Ex. No | R1 | R2 | R3 | RT/min |
|---|---|---|---|---|
| 62 | 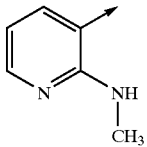 |  | 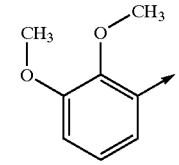 | 1.23 | a = 2-(2-fluorophenoxy)ethylamine was obtained from ChemDiv Inc. Building Blocks
b = 2-(1H-pyrazol-1-yl)ethylamine was obtained from Peakdale

EXAMPLES 63 TO 218

The following examples of general formula:

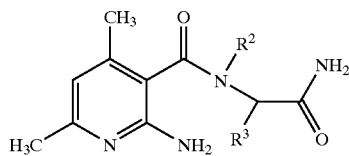

were prepared from 2-amino-4,6-dimethylnicotinic acid (obtained from Bionet Research Ltd.), the compound from preparation 6 and the appropriate amine and aldehyde, following the procedure described for the preparation of examples 25 to 62.

| Ex No | R2 | R3 | Rt/min |
|---|---|---|---|
| 63 |  | 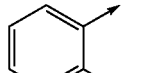 | 1.36 |
| 64 |  | 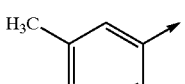 | 1.37 |
| 65 |  | 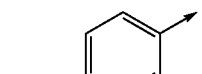 | 1.36 |
| 66 |  | 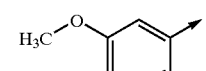 | 1.27 |
| 67 |  | 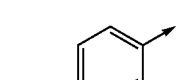 | 1.47 |
| 68 |  | 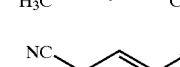 | 1.21 |
| 69 |  | 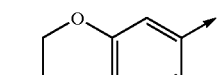 | 1.21 |
| 70 |  | 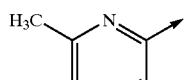 | 1.17 |
| 71 |  | 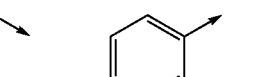 | 1.43 |
| 72 |  | 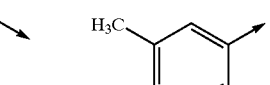 | 1.43 |
| 73 |  | 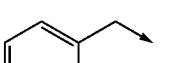 | 1.43 |
| 74 |  | 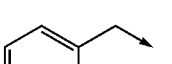 | 1.33 |
| 75 |  |  | 1.34 |
| 76 |  | 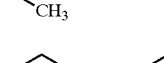 | 1.43 |
| 77 |  | 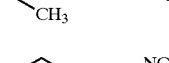 | 1.27 |

-continued

| Ex No | R2 | R3 | Rt/min |
|---|---|---|---|
| 78 | 2-CH₃-phenyl | 4-CN-phenyl | 1.29 |
| 79 | 2-CH₃-phenyl | 2-F-phenyl | 1.34 |
| 80 | 2-CH₃-phenyl | 3-F-phenyl | 1.37 |
| 81 | 2-CH₃-phenyl | 2-Cl-phenyl | 1.41 |
| 82 | 2-CH₃-phenyl | 2,3-diCH₃-phenyl | 1.5 |
| 83 | 2-CH₃-phenyl | 2,4-diCH₃-phenyl | 1.51 |
| 84 | 2-CH₃-phenyl | 3,4-diCH₃-phenyl | 1.5 |
| 85 | 2-CH₃-phenyl | 3,5-diCH₃-phenyl | 1.52 |
| 86 | 2-CH₃-phenyl | 2,4-diCH₃-phenyl | 1.57 |
| 87 | 2-CH₃-phenyl | 2-CH₃-3-F-phenyl | 1.46 |
| 88 | 2-CH₃-phenyl | 3-CN-2-F-phenyl | 1.36 |

-continued

| Ex No | R2 | R3 | Rt/min |
|---|---|---|---|
| 89 | 2-CH₃-phenyl | 2,3-diF-phenyl | 1.4 |
| 90 | 2-CH₃-phenyl | 2,6-diF-phenyl | 1.35 |
| 91 | 2-CH₃-phenyl | 2,5-diF-phenyl | 1.39 |
| 92 | 2-CH₃-phenyl | pyridin-2-yl | 1.14 |
| 93 | 2-CH₃-phenyl | pyridin-3-yl | 1.03 |
| 94 | 2-CH₃-phenyl | pyridin-4-yl | 1.03 |
| 95 | 2-CH₃-phenyl | 6-CH₃-pyridin-2-yl | 1.23 |
| 96a | 2-CH₃-phenyl | 1-CH₃-pyrazol-4-yl | 1.0 |
| 97 | 3-CH₃-phenyl | 3-CH₃-phenyl | 1.54 |
| 98 | 3-CH₃-phenyl | 4-CH₃-phenyl | 1.46 |
| 99 | 3-CH₃-phenyl | 2-F-phenyl | 1.38 |

-continued
| Ex No | R2 | R3 | Rt/min |
|---|---|---|---|
| 100 | 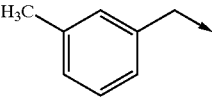 | 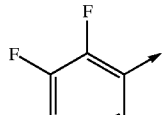 | 1.42 |
| 101 | 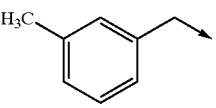 | 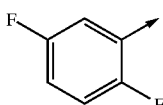 | 1.4 |
| 102 | 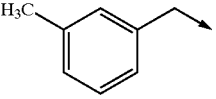 | 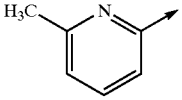 | 1.26 |
| 103 | 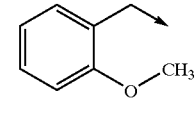 | 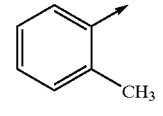 | 1.39 |
| 104 | 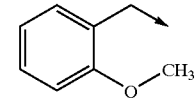 | 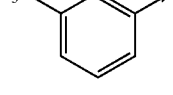 | 1.49 |
| 105 | 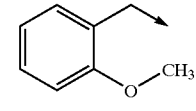 | 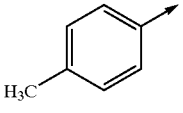 | 1.49 |
| 106 | 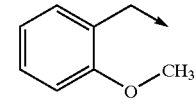 | 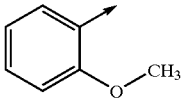 | 1.4 |
| 107 | 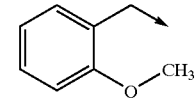 | 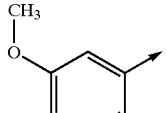 | 1.4 |
| 108 | 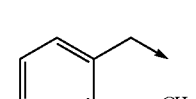 | 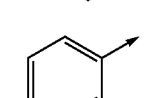 | 1.4 |
| 109 | 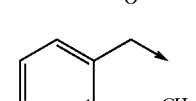 | 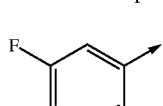 | 1.43 |
| 110 | 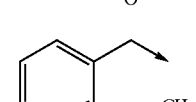 | 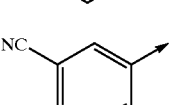 | 1.35 |
| 111 | 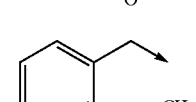 | 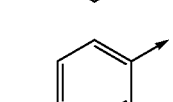 | 1.36 |
-continued
| Ex No | R2 | R3 | Rt/min |
|---|---|---|---|
| 112 | 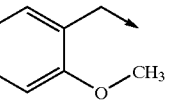 | 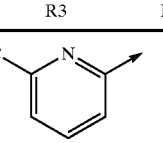 | 1.31 |
| 113 | 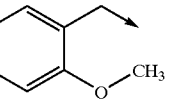 | 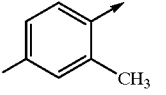 | 1.59 |
| 114 | 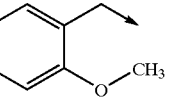 | 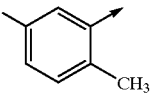 | 1.58 |
| 115 | 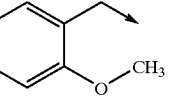 | 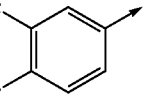 | 1.57 |
| 116 | 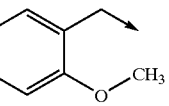 | 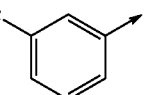 | 1.59 |
| 117 | 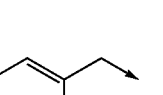 | 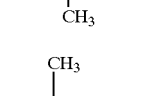 | 1.64 |
| 118 | 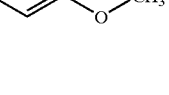 | 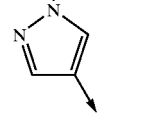 | 1.26 |
| 119 | 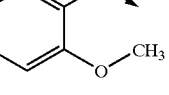 | 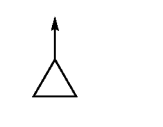 | 1.23 |
| 120 | 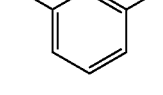 | 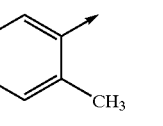 | 1.15 |
| 121 | 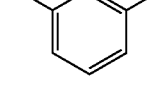 | 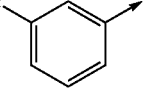 | 1.15 |
| 122 | 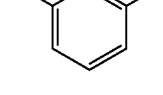 | 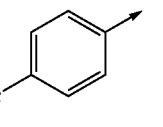 | 1.15 |
| 123 | 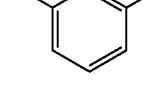 | 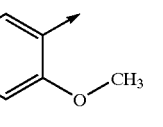 | 1.15 |

-continued

| Ex No | R2 | R3 | Rt/min |
|---|---|---|---|
| 124 | 3-MeO-C6H4-CH2- | 4-CN-C6H4- | 1.11 |
| 125 | 3-MeO-C6H4-CH2- | 2-F-C6H4- | 1.1 |
| 126 | 3-MeO-C6H4-CH2- | 3-F-C6H4- | 1.15 |
| 127 | 3-MeO-C6H4-CH2- | 2,3-diMe-C6H3- | 1.3 |
| 128 | 3-MeO-C6H4-CH2- | 3,4-diMe-C6H3- | 1.32 |
| 129 | 3-MeO-C6H4-CH2- | 6-Me-pyridin-2-yl | 1.07 |
| 130 | 4-MeO-C6H4-CH2- | 3-MeO-C6H4- | 1.23 |
| 131 | 4-MeO-C6H4-CH2- | 4-CN-C6H4- | 1.2 |
| 132 | 4-MeO-C6H4-CH2- | 3,4-diMe-C6H3- | 1.41 |
| 133 | 2,4-diMe-C6H3-CH2- | 2-Me-C6H4- | 1.2 |
| 134 | 2,4-diMe-C6H3-CH2- | 3-Me-C6H4- | 1.22 |
| 135 | 2,4-diMe-C6H3-CH2- | 2-MeO-C6H4- | 1.12 |
| 136 | 2,4-diMe-C6H3-CH2- | 3-MeO-C6H4- | 1.25 |
| 137 | 2,4-diMe-C6H3-CH2- | 3-CN-C6H4- | 1.39 |
| 138 | 2,4-diMe-C6H3-CH2- | 2-F-C6H4- | 1.45 |
| 139 | 2,4-diMe-C6H3-CH2- | 3-F-C6H4- | 1.47 |
| 140 | 2,4-diMe-C6H3-CH2- | pyridin-2-yl | 1.23 |
| 141 | 2,4-diMe-C6H3-CH2- | 6-Me-pyridin-2-yl | 1.09 |
| 142 | 3,4-diMe-C6H3-CH2- | 2-Me-C6H4- | 1.66 |
| 143 | 3,4-diMe-C6H3-CH2- | 3-Me-C6H4- | 1.67 |
| 144 | 3,4-diMe-C6H3-CH2- | 2-MeO-C6H4- | 1.55 |
| 145 | 3,4-diMe-C6H3-CH2- | 3-MeO-C6H4- | 1.56 |
| 146 | 3,4-diMe-C6H3-CH2- | 2-F-C6H4- | 1.57 |

-continued
| Ex No | R2 | R3 | Rt/min |
|---|---|---|---|
| 147 | 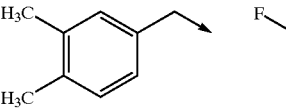 | 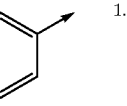 | 1.59 |
| 148 | 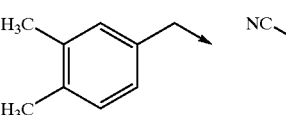 | 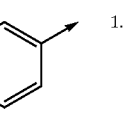 | 1.5 |
| 149 | 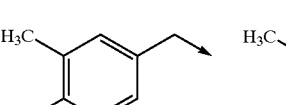 | 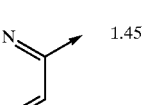 | 1.45 |
| 150 | 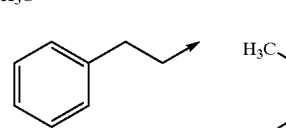 | 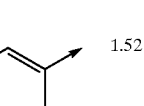 | 1.52 |
| 151 | 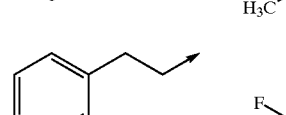 | 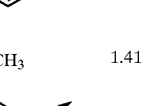 | 1.41 |
| 152 |  | 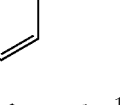 | 1.64 |
| 153 | 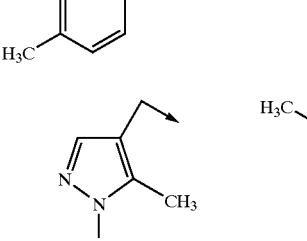 | 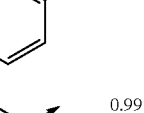 | 0.99 |
| 154 | 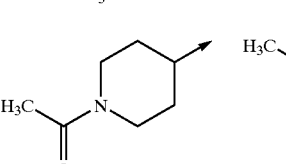 | 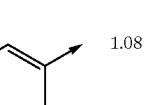 | 1.08 |
| 155 | 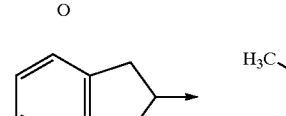 | 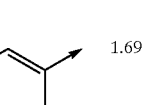 | 1.69 |
| 156 | 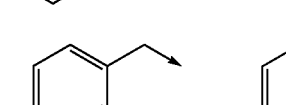 | 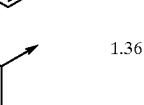 | 1.36 |
| 157 | 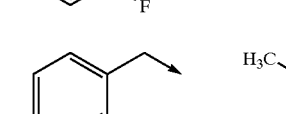 | 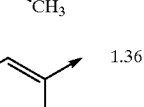 | 1.36 |
-continued
| Ex No | R2 | R3 | Rt/min |
|---|---|---|---|
| 158 | 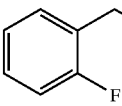 | 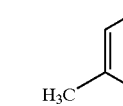 | 1.37 |
| 159 | 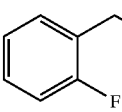 | 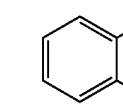 | 1.28 |
| 160 | 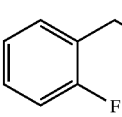 | 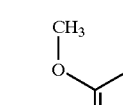 | 1.27 |
| 161 | 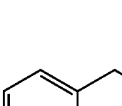 | 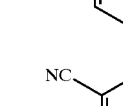 | 1.23 |
| 162 | 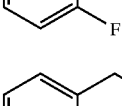 | 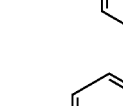 | 1.29 |
| 163 | 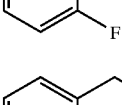 | 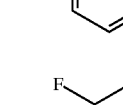 | 1.3 |
| 164 | 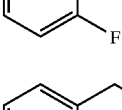 | 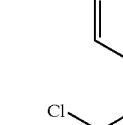 | 1.41 |
| 165 | 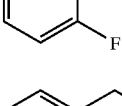 | 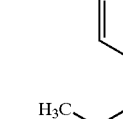 | 1.46 |
| 166 | 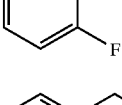 | 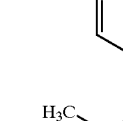 | 1.45 |
| 167 | 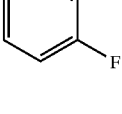 | 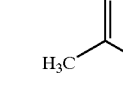 | 1.46 |
| 168 | 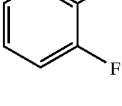 | 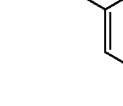 | 1.47 |

| Ex No | R2 | R3 | Rt/min |
|---|---|---|---|
| 169 | 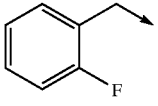 | 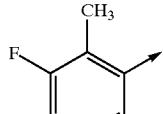 | 1.4 |
| 170 | 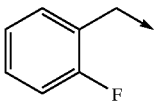 | 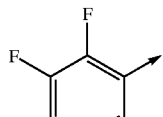 | 1.34 |
| 171 | 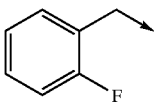 | 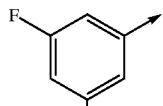 | 1.32 |
| 172 | 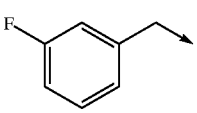 | 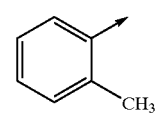 | 1.52 |
| 173 | 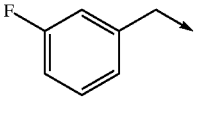 | 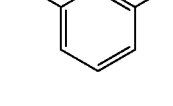 | 1.5 |
| 174 | 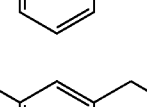 | 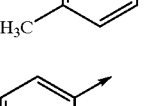 | 1.51 |
| 175 | 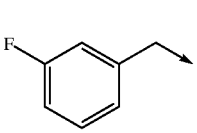 | 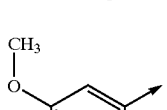 | 1.42 |
| 176 | 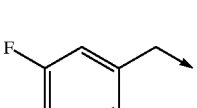 | 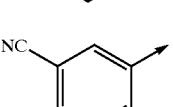 | 1.42 |
| 177 | 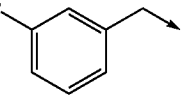 | 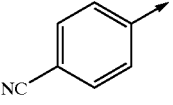 | 1.36 |
| 178 | 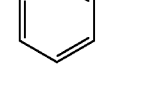 | 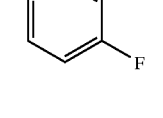 | 1.37 |
| 179 |  |  | 1.42 |
| 180 | 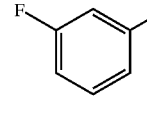 | 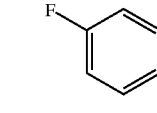 | 1.43 |
| 181 | 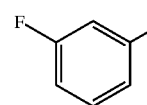 | 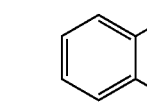 | 1.48 |
| 182 | 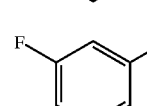 | 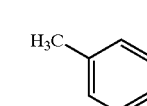 | 1.62 |
| 183 | 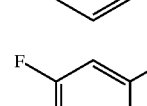 | 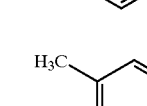 | 1.59 |
| 184 | 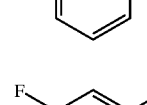 | 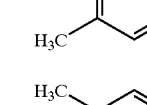 | 1.61 |
| 185 | 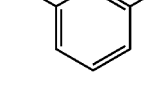 | 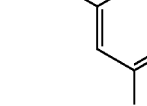 | 1.64 |
| 186 | 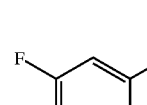 |  | 1.56 |
| 187 | 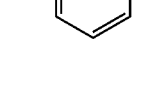 | 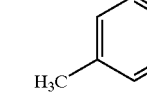 | 1.47 |
| 188 | 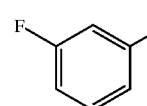 | 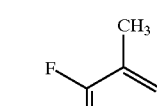 | 1.45 |
| 189 | 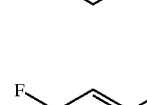 | 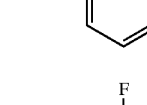 | 1.31 |
| 190 | 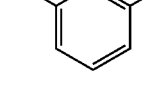 | 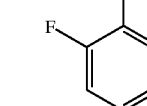 | 1.42 |

| Ex No | R2 | R3 | Rt/min |
|---|---|---|---|
| 191 | 3-F-phenyl-CH2- | pyridin-3-yl | 1.11 |
| 192 | 3-F-phenyl-CH2- | 6-methylpyridin-2-yl | 1.3 |
| 193 | 4-F-phenyl-CH2- | 2-methylphenyl | 1.4 |
| 194 | 4-F-phenyl-CH2- | 3-methylphenyl | 1.38 |
| 195 | 4-F-phenyl-CH2- | 4-methylphenyl | 1.41 |
| 196 | 4-F-phenyl-CH2- | 3-methoxyphenyl | 1.3 |
| 197 | 4-F-phenyl-CH2- | 2-cyanophenyl | 1.26 |
| 198 | 4-F-phenyl-CH2- | 3-cyanophenyl | 1.24 |
| 199 | 4-F-phenyl-CH2- | 4-cyanophenyl | 1.24 |
| 200 | 4-F-phenyl-CH2- | 2-fluoropyridin-3-yl | 1.31 |
| 201 | 4-F-phenyl-CH2- | 3-fluorophenyl | 1.32 |
| 202 | 4-F-phenyl-CH2- | 2-chlorophenyl | 1.37 |
| 203 | 4-F-phenyl-CH2- | 2,4-dimethylphenyl | 1.48 |
| 204 | 4-F-phenyl-CH2- | 2,5-dimethylphenyl | 1.46 |
| 205 | 4-F-phenyl-CH2- | 3,5-dimethylphenyl | 1.5 |
| 206 | 4-F-phenyl-CH2- | 2,4-dimethylphenyl (isomer) | 1.49 |
| 207 | 4-F-phenyl-CH2- | 2-fluoro-3-methylphenyl | 1.45 |
| 208 | 4-F-phenyl-CH2- | 2,3-difluorophenyl | 1.35 |
| 209 | 4-F-phenyl-CH2- | 2,6-difluorophenyl | 1.2 |
| 210 | 4-F-phenyl-CH2- | 2,5-difluorophenyl | 1.33 |
| 211 | 4-F-phenyl-CH2- | 2-cyano-4-fluorophenyl | 1.3 |
| 212 | 4-F-phenyl-CH2- | 6-methylpyridin-2-yl | 1.19 |
| 213 | 4-F-phenyl-CH2- | 1-methyl-1H-pyrazol-4-yl | 0.96 |

-continued

| Ex No | R2 | R3 | Rt/min |
|---|---|---|---|
| 214 | 3-Cl-benzyl | 2-methylphenyl | 1.49 |
| 215 | 3-Cl-benzyl | 3-methylphenyl | 1.48 |
| 216 | 3-Cl-benzyl | 3-fluorophenyl | 1.42 |
| 217 | 3-Cl-benzyl | 3-cyanophenyl | 1.32 |
| 218 | 3-Cl-benzyl | 6-methylpyridin-2-yl | 1.28 | a = 1-methyl-1H-pyrazole-4-carbaldehyde was obtained from ChemCollect

EXAMPLES 219 TO 233

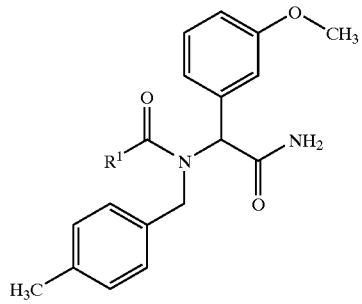

Solutions of 4-methylbenzylamine (100 μl, 0.5M in methanol) and m-anisaldehyde (100 μl, 0.5M in methanol) were added to a solution of the appropriate acids (100 μl, 0.5M methanol/1-methyl-2-pyrrolidinone 1:1). A solution of the isocyanate from preparation 6 (100 μl, 0.5M in methanol/cyclohexane, 1:1) was then added, the reactions sealed and heated at 50° C. for 24 hours. The solvents were removed under reduced pressure, hydrochloric acid in tetrahydrofuran (500 μl, 0.6M) was added, and the vessels were resealed and agitated again at room temperature for a further 24 hours. The solvents were removed under reduced pressure, the residues dissolved in methyl sulphoxide, and purified by HPLC, using a Phenomonex Luna 150×10 mm, 10 am column, in acetonitile: 0.1% aqueous diethylamine, at 8 mlmin$^{-1}$, at 225 nM, using the following gradient.

| Time (min) | % acetonitrile |
|---|---|
| 0.00–0.50 | 5 |
| 0.50–0.60 | 5–20 |
| 0.60–6.50 | 20–95 |

| Ex. No. | R1 | Retention time/min |
|---|---|---|
| 219 | 2-methylpyridin-3-yl | 5.366 |
| 220 | 4-trifluoromethylpyridin-3-yl | 5.391 |
| 221a | 4-trifluoromethylpyridin-3-yl | 5.279 |
| 222 | 6-trifluoromethylpyridin-3-yl | 5.838 |
| 223 | 2-ethoxypyridin-3-yl | 5.265 |
| 224b | 2-propoxypyridin-3-yl | 5.782 |
| 225 | 6-chloropyridin-3-yl | 5.559 |
| 226 | 2-chloropyridin-4-yl | 4.693 |
| 227 | 5-bromopyridin-3-yl | 4.749 |
| 228 | 2-aminopyridin-4-yl | 5.321 |

-continued

| Ex. No. | R1 | Retention time/min |
|---|---|---|
| 229 | 2-chloro-6-methylpyridin-3-yl | 4.777 |
| 230 | quinolin-2-yl | 5.642 |
| 231 | quinolin-3-yl | 5.321 |
| 232 | pyrazin-2-yl | 5.670 |
| 233c | 5-chloro-2-methylsulphanyl-pyrimidin-4-yl | 4.832 | a = (4-trifluoromethyl)nicotinic acid obtained from Maybridge
b = starting nicotinic acid prepared as in WO 9954333
c = 5-chloro-2-methylsulphanyl-pyrimidine-4-carboxilic acid obtained from Maybridge

EXAMPLE 234

N-[2-Amino-1-(3-methoxyphenyl)-2-oxoethyl]-4-cyano-N-(4-methylbenzyl)benzamide

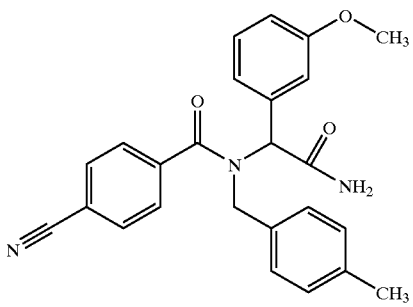

A mixture of 4-cyanobenzoic acid (584 mg, 4 mmol), m-anisaldehyde (486 μl, 4 mmol), 4-methylbenzylamine (509 μl, 4 mmol) and the compound from preparation 6 (752 mg, 4 mmol) in methanol (15 ml) was stirred at room temperature for 18 hours. The reaction was then stirred at 50° C. for a further 4 hours, and the mixture concentrated under reduced pressure. The residue was dissolved in a solution of hydrochloric acid in tetrahydrofuran (0.6N, 15 ml), and the solution stirred at room temperature for 2 hours, then evaporated under reduced pressure. The product was washed with 1N sodium hydroxide solution, and extracted with ethyl acetate. The combined organic extracts were washed with brine, dried ($MgSO_4$) and evaporated under reduced pressure. The crude product was purified by column chromatography on silica gel using methanol:dichloromethane (1:99) as eluant to afford the title compound as a yellow foam, 1.38 g.

$^1$Hnmr ($CDCl_3$, 400 MHz): □ 2.27 (s, 3H), 3.75 (s, 3H), 4.35 (bd, 1H), 4.58 (bd, 1H), 5.43–5.70 (m, 3H), 6.88 (m, 4H), 6.99 (m, 3H), 7.22 (m, 2H), 7.50–7.63 (m, 3H).

LRMS: m/z ($ES^+$) 436 [$MNa^+$]

Microanalysis found: C, 71.63; H, 5.66; N, 10.05. $C_{25}H_{23}N_3O_3$; $0.3H_2O$ requires C, 71.69; H, 5.68; N, 10.03%.

EXAMPLES 235 TO 239

The following compounds of general formula:

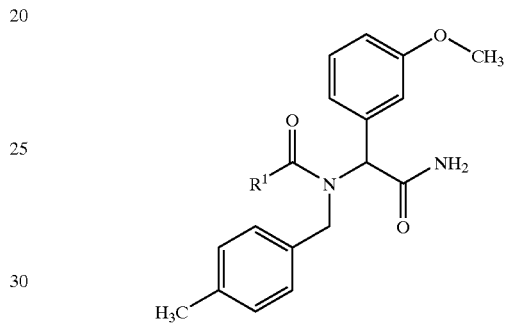

were prepared from m-anisaldehyde, 4-methylbenzylamine, the compound from preparation 6 and the appropriate acid, following a similar procedure to that described in example 234.

| Ex. No. | R1 | Yield/% | |
|---|---|---|---|
| 235 | 2,6-difluorophenyl | 30 | $^1$Hnmr ($CDCl_3$, 400 MHz) □: 2.25(s, 3H), 3.75(s, 3H), 4.38(d, 1H), 4.58(d, 1H), 5.40–5.60(m, 3H), 6.84(m, 4H), 7.00(m, 4H), 7.24(m, 3H). LRMS: m/z ($ES^+$) 447 [$MNa^+$] Microanalysis found: C, 67.62; H, 5.21; N, 6.51. $C_{24}H_{22}F_2N_2O_3$ requires C, 67.92; H, 5.22; N, 6.60%. |
| 236 | 2,4-difluorophenyl | 68 | $^1$Hnmr ($CDCl_3$, 400 MHz) □: 2.24(s, 3H), 3.78(s, 3H), 4.36(d, 1H), 4.58(d, 1H), 5.50(bs, 2H), 6.78–7.02(m, 10H), 7.25(m, 2H). HRMS: m/z($ES^+$) 849.3238 [$2M + H$]$^+$ $C_{24}H_{22}F_2N_2O_3$ requires 849.3269 |
| 237 | 2,6-difluoro-4-methoxyphenyl | 20 | $^1$Hnmr ($CDCl_3$, 400 MHz) □: 2.23(s, 3H), 3.78(2xs, 6H), 4.38(d, 1H), 4.59(d, 1H), 5.57(s, 1H), 6.42(m, 2H), 6.66(m, 3H), 7.00(m, 4H), 7.24(m, 1H). LRMS: m/z($ES^+$) 477 [$MNa^+$] |

57

-continued

| Ex. No. | R1 | Yield/% | |
|---|---|---|---|
| 238 | 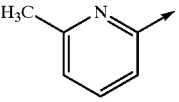 | 85 | ¹Hnmr (DMSOd₆, 400 MHz) (rotamers) $\square$: 2.12, 2.18(2xs, 3H), 2.40, 2.58 (2xs, 3H), 3.64(s, 3H), 4.25, 4.43(2xd, 1H), 4.79, 4.90(2xd, 1H), 5.82, 5.99 (2xs, 1H), 6.64–6.96(m, 7H), 7.08–7.23(m, 3H), 7.37, 7.59, 7.82(3xm, 3H). Microanalysis found: C, 71.21; H, 6.32; N, 10.22. $C_{24}H_{25}N_3O_3$ requires C, 71.44; H, 6.25; N, 10.41% |
| 239a | 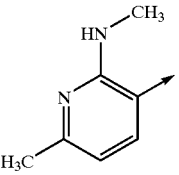 | 25 | ¹Hnmr (DMSOd₆, 400 MHz) $\square$: 2.16(s, 3H), 2.22 (s, 3H), 2.84(s, 3H), 3.58 (s, 3H), 4.16(d, 1H), 4.40 (d, 1H), 5.80(s, 1H), 6.30 (d, 1H), 6.60(m, 3H), 6.78 (m, 1H), 6.81(m, 3H), 7.16 (m, 1H), 7.19(d, 1H), 7.41 (s, 1H), 7.60(s, 1H). LRMS: m/z(ES⁺) 455 [MNa⁺] | a = 6-methyl-2-methylamino-nicotinic acid was obtained from Peakdale

EXAMPLE 240

N-[3-Amino-1-(3-methoxyphenyl)-3-oxopropyl]-4-methyl-N-(4-methylbenzyl)nicotinamide

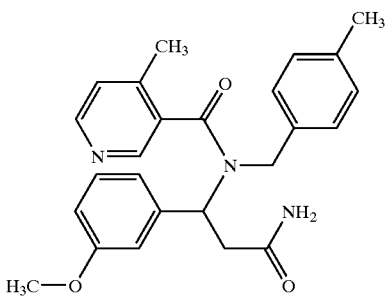

A solution of the acid from preparation 13 (176 mg, 0.42 mmol), O-(1H-benzotriazol-1-yl)-N,N,N',N'-tetramethyluronium hexafluorophosphate (157 mg, 0.42 mol) and N-ethyldiisopropylamine (147 µl, 0.84 mmol) in dichloromethane (20 ml) was stirred at room temperature for an hour. 0.88 Ammonia (0.5 ml) was added and the reaction stirred at room temperature for 18 hours. The mixture was washed with sodium bicarbonate solution (20 ml), water (20 ml) and brine (20 ml) then dried (Na₂SO₄) and evaporated under reduced pressure. The residue was purified by column chromatography on silica gel using an elution gradient of dichloromethane:methanol: 0.88 ammonia (100:0:0 to 97.5:2.5:0.25) to afford the title compound, 79 mg.

HRMS: m/z (ES⁺) 418.2117 [MH⁺]

EXAMPLE 241

2-Amino-N-[(1S)-3-amino-3-oxo-1-phenylpropyl]-N-(4-methylbenzyl)nicotinamide

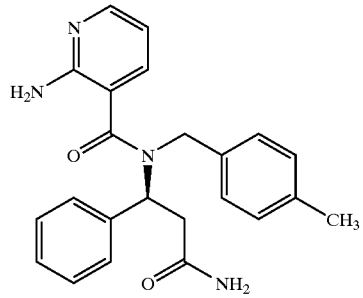

The amine from preparation 11 (100 mg, 0.37 mmol), 2-aminonicotininc acid (47.1 mg, 0.34 mmol) and O-(1H-benzotriazol-1-yl)-N,N,N',N'-tetramethyluronium hexafluorophosphate (141 mg, 0.37 mol) were added to a solution of N-ethyldiisopropylamine (195 µl, 1.125 mmol) in N,N-dimethylformamide (2 ml), and the solution stirred at room temperature for 18 hours, then at 85° C. for a further 48 hours. The cooled mixture was concentrated under reduced pressure and the residue partitioned between sodium carbonate solution (10 ml) and ethyl acetate (10 ml). The layers were separated, the organic phase washed with water (10 ml) and brine (5 ml), dried (Na₂SO₄) and evaporated under reduced pressure. The residual brown oil was purified by column chromatography on silica gel using an elution gradeint of dichloromethane:methanol (100:0 to 90:10) to afford the title compound as a brown oil, 25.1 mg.

¹H-nmr (CDCl₃, 400 MHz) δ: 2.21 (s, 3H), 2.64 (m, 1H), 3.19 (m, 1H), 4.21 (m, 1H), 4.58 (m, 1H), 5.80–6.05 (m, 2H), 6.38–6.72 (m, 3H), 7.25 (m, 9H), 7.95 (s, 1H).

HRMS: m/z (ES⁺) 389.1972 [MH⁺] $C_{23}H_{24}N_4O_2$ requires 389.1972.

EXAMPLE 242

5-Chloro-2-methylthio-N-[2-amino-1-{1,4-benzodioxan-6-yl}-2-oxoethyl]-N-(4-methylbenzyl) pyrimidine-4-carboxamide

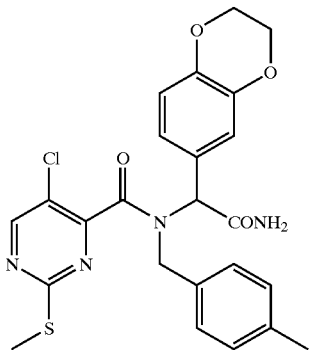

To a solution of methyl-5-chloro-2-methylthiopyrimidine-4-carboxylate (1.0 g, 4.88 mmol) in methanol (40 ml) was added 4-methylbenzylamine (0.71 g, 5.86 mmol), 1,4 benzodioxan-6-carboxaldehyde (0.96 g, 5.86 mmol) and 4-phenylcyclohex-1-enylisonitrile (1.075 g, 5.86 mmol). After 3 hours the solvent was evaporated and the residue was dissolved in 10 ml of 1.2N HCl in THF. After 1 hour the solvent was evaporated and the residue dissolved in ethyl acetate (100 ml). This solution was washed with water (50 ml), saturated NaHCO₃ solution (50 ml) and brine (50 ml), dried over MgSO₄, filtered and evaporated. The residue was purified by chromatography on silica gel (50 gm), eluting with a gradient of pentane-ethyl acetate (9:1 to 4:6 in 10% increments of EtOAc) to afford the title compound as a solid, 2.28 g, (93%).

¹Hnmr (CDCl₃, 400 MHz) δ: 2.2 (s, 3H), 2.8 (s, 3H), 4.1–4.5 (m, 6H), 5.0–5.2 (m, 1H), 5.5–5.8 (m, 2H), 6.5–7.3 (m, 3H), 8.3 (s, 1H)

LRMS: m/z (APCI+) 521 [MNa⁺]

Microanalysis found: C, 57.20; H, 4.70; N, 10.81. C₂₄H₂₃ClN₄O₄S requires C, 57.77; H, 4.65; N, 11.23%

EXAMPLE 243

5-Chloro-2-methanesulfonyl-N-[2-amino-1-{1,4-benzodioxan-6-yl}-2-oxoethyl]-N-(4-methylbenzyl)pyrimidine-4-carboxamide

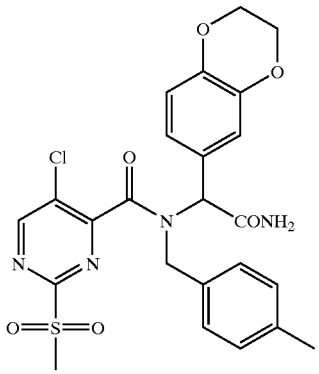

To a solution of the sulfide from example 242 (2.04 g, 4.08 mmol) in CH₂Cl₂ (30 ml) was added 3-chloroperoxybenzoic acid (3.10 g, 8.99 mmol) portionwise over 10 minutes at ambient temperature. After 18 hours the solution was washed with 10% NaHSO₃ solution (10 ml), saturated NaHCO₃ solution (2×10 ml), brine (10 ml), dried over MgSO₄, filtered and evaporated to give the title compound as a yellow solid, 1.5 g, (69%).

¹Hnmr (CDCl₃, 400 MHz) δ: 2.2 &2.38 (2×s, 3H), 3.2 & 3.38 (2×s, 3H) 4.1–4.6 (m, 6.5H), 5.15–5.25 (m, 0.5H), 5.4–5.8 (br m, 1H), 6.05 (s, 1H) 6.7–7.3 (m, 7H), 8.6 & 8.7(2×s, 1H)

LRMS: m/z (APCI⁺) 531 [MH⁺]

EXAMPLE 244

5-Chloro-2-ethylamino-N-[2-amino-1-{1,4-benzodioxan-6-yl}-2-oxoethyl]-N-(4-methylbenzyl)pyrimidine-4-carboxamide

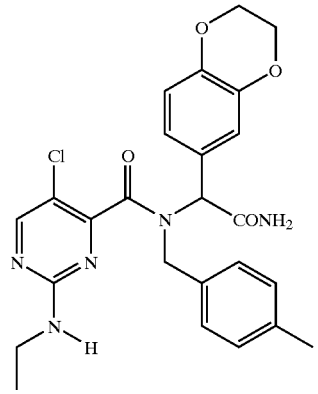

Ethylamine was passed through an ice-cold solution of the sulfone from example 243 (0.15 g, 0.28 mmol) in THF (3 ml) for 20 minutes. After 2 hours at room temperature, the solvent was evaporated. The residue was dissolved in ethyl acetate (10 ml) and the solution was washed with water (10 m[), saturated NaHCO₃ solution (2×10 ml), brine (10 ml), dried over MgSO₄, filtered and evaporated. The residue was chromatographed on silica gel (10 g) eluting with a gradient of pentane-ethyl acetate from 90110 to 30/70 in 10% increments of ethyl acetate to give the title compound as a foam 107 mg, (76%).

¹Hnmr (CDCl₃, 400 MHz) δ: 1.15–1.3 (complex t, 3H), 2.25 & 2.30 (2×s, 3H), 3.3–3.45 (complex q, 2H) 4.1–4.6 (m, 5.5H), 4.9–5.00 (m, 0.5H), 5.2–6.0 (m's, 3H), 6.6–7.2 (m, 7H), 8.15 & 8.2 (2×s, 1H)

LRMS: m/z (APCI⁺) 518 [MNa⁺]

Microanalysis found: C, 59.76; H, 5.36; N, 13.63. C₂₅H₂₆ClN₅O₄, 0.05 CH₂Cl₂ requires C, 60.15; H, 5.26; N, 14.00%

EXAMPLE 245

5-Chloro-2-amino-N-[2-amino-1-f 1,4-benzodioxan-6-yl]-2-oxoethyl]-N-(4-methylbenzyl)pyrimidine-4-carboxamide

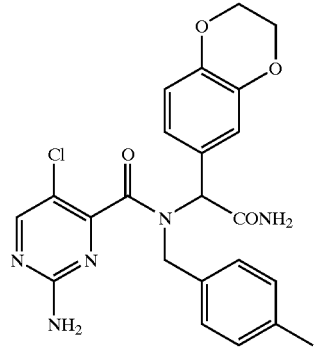

The title compound was obtained from the sulfone of example 243, using the method from example 244 and using ammonia as the amine, as a foam, 91.5 mg, (89%)

¹Hnmr (CDCl₃, 400 MHz) δ: 2.25 & 2.30 (2×s, 3H), 4.1–4.6 (m, 5.5H), 4.9–4.95 (d, 0.5H), 5.2–6.0 (m's, 5H), 6.6–7.2 (m, 7H), 8.15 & 8.2 (2×s, 1H)

LRMS: m/z (APCI⁺) 468 [MH⁺]

Microanalysis found: C, 57.25; H, 4.80; N, 14.14. $C_{23}H_{22}ClN_5O_4$, 0.2 $CH_2Cl_2$ requires C, 57.47; H, 4.68; N, 14.44%

EXAMPLE 246

5-Chloro-2-aminoethylamino-N-[2-amino-1-{1,4-benzodioxan-6-yl}-2-oxoethyl]-N-4-methylbenzyl)pyrimidine-4-carboxamide

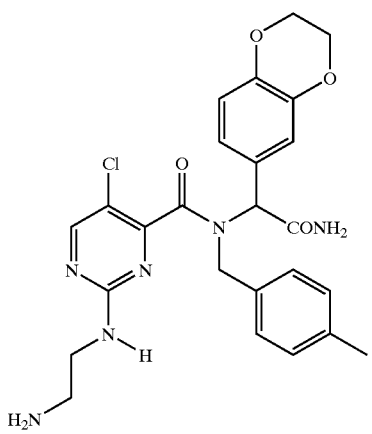

To an ice-cold solution of the product from preparation 14 (276 mg, 0.45 mmol) and anisole (245 mg, 2.26 mmol) in $CH_2Cl_2$ (6 ml) was added trifluoroacetic acid (6 ml), After 2 hrs the reaction mixture was evaporated to dryness. The residue was dissolved in fresh $CH_2Cl_2$ (20 ml) and the solution was washed with 10% $Na_2CO_3$ solution (20 ml), saturated $NaHCO_3$ solution (20 ml), brine (20 ml), dried over $MgSO_4$, filtered and evaporated. The residue was purified by chromatography on silica gel (10 gm), eluting with a gradient of $CH_2Cl_2$—$CH_3OH$—$NH_4OH$ (99:1:0.1 to 90:10:1 in 1% increments of $CH_3OH$ and 0.1% increments of $NH_4OH$) to afford the title compound as a foam, 69 mg, (30%).

¹Hnmr (CDCl₃, 400 MHz) δ: 1.95–2.6 (s @ 2.3, 3H & br s, 2H), 2.9–3.1 (m, 2H), 3.4–3.65 (m, 2H), 4.1–4.8 (m, 6H), 5.25 & 5.5 (2×s, 1H), 5.7–6.4 (m, 2H), 6.6–7.1 (m, 7H), 8.1 &8.2 (2×s, 1H)

LRMS: m/z (APCI⁺) 511 [MH⁺]

Microanalysis found: C, 56.68; H, 5.40; N, 15.34. $C_{25}H_{27}ClN_6O_4$: 0.25 $CH_2Cl_2$ requires C, 56.98; H, 5.21; N, 15.79%

EXAMPLE 247

5-Chloro-2-methylthio-N-[2-amino-1-{3-methoxyphenyl}-2-oxoethyl]-N-(4-methylbenzyl)pyrimidine-4-carboxamide

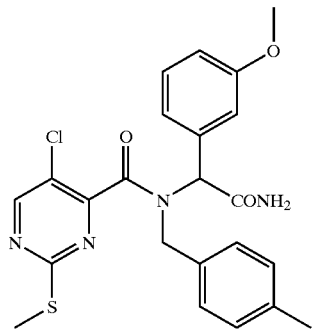

This was prepared in the same manner as the product from example 242, using 3-methoxybenzaldehyde as the aldehyde component, to return the title compound as a solid, 1.74 g, (76%).

¹Hnmr (CDCl₃, 400 MHz) δ: 2.25 & 2.35 (2×s, 3H), 2.38 & 2.50(2×s, 3H), 3.65 & 3.78 (2×s, 3H) 4.35–4.6 (q, 2H), 5.8 (s, 1H), 6.8–7.3 (m, 8H), 8.4 (s, 1H)

LRMS: m/z (APCI⁺) 471/473 [MH⁺]

Microanalysis found: C, 57.34; H, 5.11; N, 11.36. $C_{23}H_{23}ClN_4O_3S$: 0.2$CH_2Cl_2$ requires C, 57.48; H, 4.86; N, 11.58%

EXAMPLE 248

5-Chloro-2-methanesulfonyl-N-[2-amino-1-{3-methoxyphenyl}-2-oxoethyl]-N-(4-methylbenzyl)pyrimidine-4-carboxamide

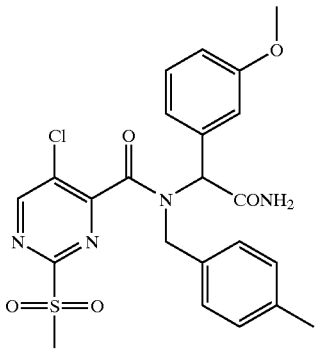

This was prepared in the same manner as the product of example 243, using the sufide from example 247, to return the title compound as a foam, 0.979, (53%).

¹Hnmr (CDCl₃, 400 MHz) δ: 2.2 &2.38 (2×s, 3H), 3.25 & 3.35 (2×s, 3H) 3.63 & 3.8 (2×s, 3H), 4.35–4.62 (q, 2H), 5.3 & 6.1 (2×s, 1H), 5.5–5.9 (br d, 2H) 6.7–7.3 (m, 8H), 8.65 (s, 1H)

LRMS: m/z (APCI⁺) 503/505 [MH⁺]

Microanalysis found: C, 53.25; H, 4.47; N, 10.50. $C_{23}H_{23}ClN_4O_5S$, 0.25$CH_2Cl_2$ requires C, 52.67; H, 4.42; N, 10.68%

EXAMPLE 249

5-Chloro-2-amino-N-[2-amino-1-{3-methoxyphenyl}-2-oxoethyl]-N-(4-methylbenzyl)pyrimidine-4-carboxamide

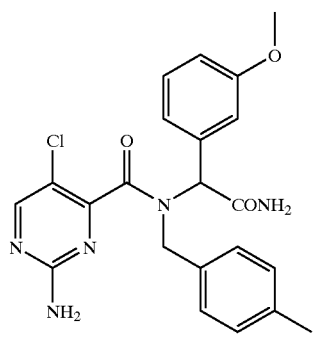

The title compound was prepared from the sulfone of example 248, using the method from example 244 and ammonia as the amine, to return the title compound as a foam, 22 mg, (12%)

¹Hnmr (CDCl₃, 400 MHz) δ: 2.25 & 2.30 (2×s, 3H), 3.65 & 3.78 (2×s, 3H), 4.3–4.6 (m, 1.75H), 4.95–5.05 (d, 0.25H), 5.4–6.0 (m's, 5H), 6.6–7.3 (m, 8H), 8.15 & 8.18(2×s, 1H)

LRMS: m/z (APCI⁺) 462⁄464 [MNa⁺]

EXAMPLE 250

5-Chloro-2-dimethylamino-N-[2-amino-1-{3-methoxyphenyl}-2-oxoethyl]-N-(4-methylbenzyl)pyrimidine-4-carboxamide

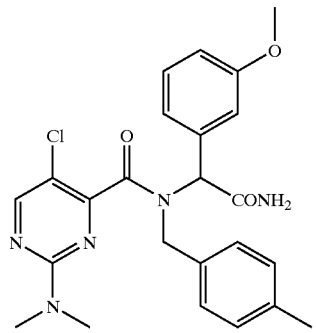

This was prepared in the same manner as the product of example 249, using dimethylamine as the amine, to give the title compound as a foam, 0.06 g, (31%).

¹Hnmr (CDCl₃, 400 MHz) δ: 2.25 & 2.30 (2×s, 3H), 3.1 & 3.18 (2×s, 6H), 3.65 & 3.75 (2×s, 3H), 4.30–4.6 (m, 1.75H), 4.90–5.00 (d, 0.25H), 5.39 & 5.59 (2×s, 1H), 5.3–5.65 (br m, 1H), 5.8–6.1 (br m, 1H), 6.7–7.3 (m, 8H), 8.2 & 8.25 (2×s, 1H)

LRMS: m/z (APCI+) 468/470 [MH⁺]

EXAMPLE 251

5-Chloro-2-methylamino-N-[2-amino-1-{3-methoxyphenyl}-2-oxoethyl]-N-(4-methylbenzyl)pyrimidine-4-carboxamide

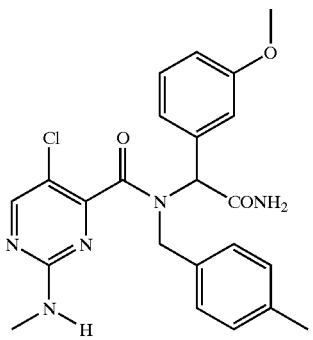

This was prepared in the same manner as the product of example 249, using methylamine as the amine, to give the title compound as a foam, 0.24 g, (88%).

¹Hnmr (CDCl₃, 400 MHz) δ: 2.25 & 2.30 (2×s, 3H), 2.9–3.0 (m, 3H), 3.65 & 3.78 (2×s, 3H), 4.35–4.6 (m, 1.75H), 4.98–5.05 (d, 0.25H), 5.2–6.00 (m, 3H), 6.6–7.3 (m, 8H), 8.1–8.2 (br s, 1H)

LRMS: m/z (APCI⁺) 454⁄456 [MH⁺]

Microanalysis found: C, 59.51; H, 5.44; N, 14.34. C₂₃H₂₄ClN₅O₃: 0.2 CH₂Cl₂ requires C, 59.17; H, 5.22; N, 14.87%

EXAMPLE 252

5-Methyl-2-methylthio-N-[2-amino-1-{3-methoxyphenyl}-2-oxoethyl]-N-(4-methylbenzyl)pyrimidine-4-carboxamide

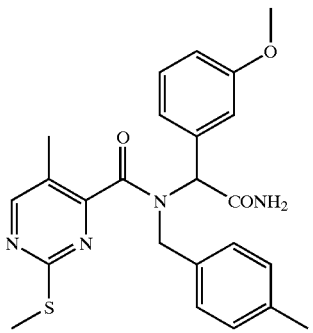

This was prepared in the same manner as the product from example 242 using 5-methyl-2-methylthiopyrimidine-4-carboxylic acid (preparation 17) and 3-methoxybenzaldehyde as the acid and aldehyde components to give the title compound as a solid, 0.97 g, (72%).

¹Hnmr (CDCl₃, 400 MHz) δ: 2.0–2.2 (m, 6H), 2.4 & 2.55 (2×s, 3H), 3.6 & 3.65 (2×s, 3H), 4.3–4.5 (m, 1.5H), 4.95–5.0 (d, 0.5H), 5.3 (s, 0.5H), 6.05 (s, 0.5H), 6.6–7.4 (m, 9.5H), 7.6–7.7 (br s, 0.5H), 8.35 (s, 0.5H), 8.62 (s, 0.5H)

LRMS: m/z (APCI⁺) 451 [MH⁺]

Microanalysis found: C, 63.31; H, 5.98; N, 11.98. C₂₄H₂₆N₄O₃S: 0.2H₂O, 0.1 EtOAc requires C, 63.30; H, 5.92; N, 12.10%

EXAMPLE 253

5-Methyl-2-methanesulfonyl-N-[2-amino-1-{3-methoxyphenyl}-2-oxoethyl]-N-(4-methylbenzyl)pyrimidine-4-carboxamide

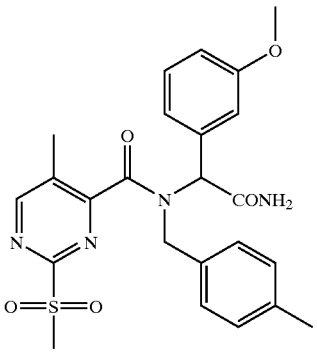

This was prepared in the same manner as the product of example 243, using the sulfide from example 252, to give the title compound as a solid, 0.7 g, (74%).

$^1$Hnmr (CDCl$_3$, 400 MHz) δ: 2.1 (s, 3H), 2.18 & 2.35 (2×s, 3H), 3.25 & 3.40 (2×s, 3H), 3.6 & 3.65 (2×s, 3H), 4.25–4.5 (q, 1.5H), 4.95–5.0 (d, 0.5H), 5.28 (s, 0.5H), 6.15 (s, 0.5H), 6.58–7.4 (m, 9.5H), 7.6–7.75 (br s, 0.5H), 8.75 (s, 0.5H), 9.1 (s, 0.5H)

LRMS: m/z (APCI$^+$) 483 [MH$^+$]

Microanalysis found: C, 59.27; H, 5.36; N, 11.48. C$_{24}$H$_{26}$N$_4$O$_5$S requires C, 59.79; H, 5.43; N, 11.61%

EXAMPLE 254

5-Methyl-2-dimethylamino-N-[2-amino-1-{3-methoxyphenyl}-2-oxoethyl]-N-(4-methylbenzyl)pyrimidine-4-carboxamide

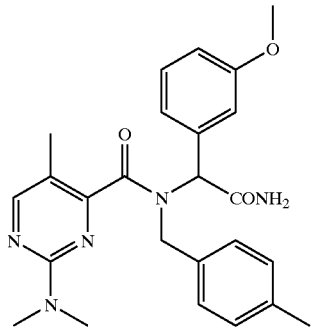

This was prepared in the same manner as the product of example 244, using the sulfone from example 253 and dimethylamine as the amine, to give the title compound as a foam, 0.14 g, (74%).

$^1$Hnmr (CDCl$_3$, 400 MHz) δ: 2.05 (s, 3H), 2.25 & 2.30 (2×s, 3H), 3.1 & 3.18 (2×s, 6H), 3.65 & 3.75 (2×s, 3H), 4.30–4.6 (m, 1.75H), 4.90–4.95 (d, 0.25H), 5.5–5.65 (m, 2H), 5.9–6.05 (br m, 1H), 6.65–7.2 (m, 8H), 8.1 & 8.15 (2×s, 1H)

LRMS: m/z (APCI$^+$) 448 [MH$^+$]

Microanalysis found: C, 65.62; H, 6.62; N, 14.75. C$_{25}$H$_{29}$N$_5$O$_3$: 0.10 CH$_2$Cl$_2$. 0.2 EtOAc requires C, 65.68; H, 6.58; N, 14.79%

EXAMPLE 255

5-Methyl-2-methylamino-N-[2-amino-1-{3-methoxyphenyl}-2-oxoethyl]-N-(4-methylbenzyl)pyrimidine-4-carboxamide

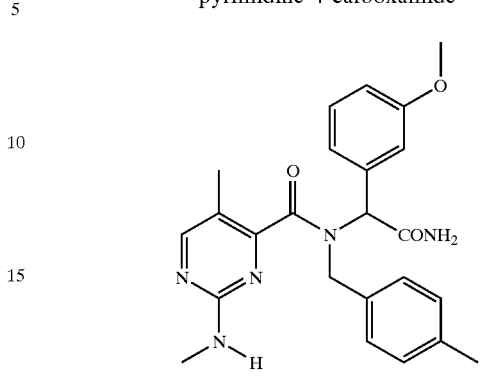

This was prepared in the same manner as the product from example 254, using methylamine as the amine, to give the title compound as a foam, 0.15 g, (85%).

$^1$Hnmr (CDCl$_3$, 400 MHz) δ: 2.0–2.15 (m, 3H), 2.25 & 2.30 (2×s, 3H), 2.9–3.0 (m, 3H), 3.65 & 3.75 (2×s, 3H), 4.35–4.6 (m, 1.75H), 4.98–5.05 (d, 0.25H), 5.2–5.35 (m, 1H), 5.5 (s, 0.25H), 5.62 (s, 0.75H), 5.7–6.1 (br m, 2H), 6.6–7.3 (m, 8H), 8.02 & 8.05 (2×s, 1H)

LRMS: m/z (APCI$^+$) 434 [MH$^+$]

Microanalysis found: C, 64.50; H, 6.32; N, 15.22. C$_{24}$H$_{27}$N$_5$O$_3$: 0.15 CH$_2$Cl$_2$ requires C, 65.00; H, 6.17; N, 15.69%

EXAMPLE 256

3-Methyl-N-[2-amino-1-{3-methoxyphenyl}-2-oxoethyl]-N-(4-methylbenzyl)pyrazine-2-carboxamide

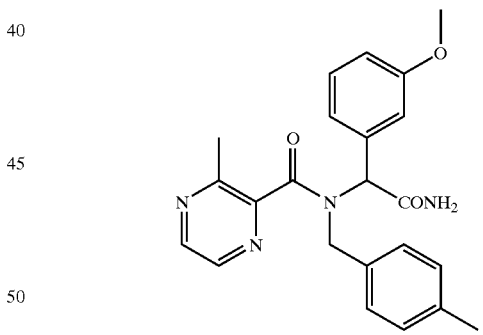

This was prepared in the same manner as the product from example 242 using 3-methylpyrazine-2-carboxylic acid (JOC, 2002, p556) and 3-methoxybenzaldehyde as the acid and aldehyde components to give the title compound as a foam, 0.5 g, (63%).

$^1$Hnmr (CDCl$_3$, 400 MHz) δ: 2.20 & 2.32 (2×s, 3H), 2.4 & 2.55 (2×s, 3H), 3.65 & 3.78 (2×s, 3H), 4.30–4.6 (m, 1.80H), 5.10–5.15 (d, 0.20H), 5.45 & 5.85 (2×s, 1H), 5.5–5.70 (br m, 1H), 5.9–6.05 (br m, 1H), 6.5–7.3 (m, 8H), 8.3–8.45 (m, 1H)

LRMS: m/z (APCI$^+$) 405 [MH$^+$]

Microanalysis found: C, 67.23; H, 6.09; N, 13.40. C$_{23}$H$_{24}$N$_4$O$_3$: 0.25H$_2$O, 0.1 EtOAc requires C, 67.27; H, 6.10; N, 13.41%

EXAMPLE 257

2-Amino-N-[carbamoyl-(2,3-dihydro-benzo[1.4]dioxin-6-yl)-methyl]-4,6-dimethyl-N-(4-methyl-benzyl)-nicotinamide

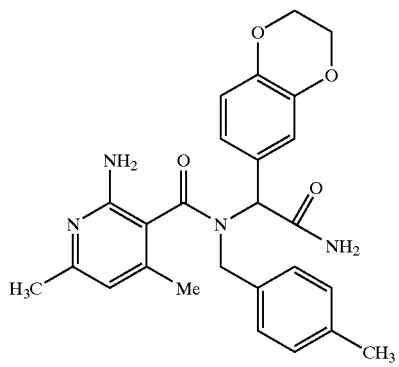

A mixture of 2-amino-4,6-dimethylnicotinic acid (obtained from Bionet Research Ltd.), (665 mg, 4 mmol), 1,4-benzodioxan-6-carboxaldehyde (656 mg, 4 mmol), 4-methylbenzylamine (509 µl, 4 mmol) and the compound from preparation 6 (752 mg, 4 mmol) in methanol (15 ml) was stirred at room temperature for 18 hours. The reaction was then stirred at 50° C. for a further 4 hours, and the mixture concentrated under reduced pressure. The residue was dissolved in a solution of hydrochloric acid in tetrahydrofuran (0.6N, 15 ml), and the solution stirred at room temperature for 4 hours, then evaporated under reduced pressure. The product was washed with 2N sodium hydroxide solution, and extracted with ethyl acetate. The combined organic extracts were washed with brine, dried ($MgSO_4$) and evaporated under reduced pressure. The crude product was purified by column chromatography on silica gel using methanol:dichloromethane (4:96) as eluant to afford a yellow foam which was triturated with diethyl ether to give the title compound as a yellow powder, 360 mg.

LRMS: m/z ($ES^+$) 461 [$MH^+$], 483 [$MNa^+$]

Microanalysis found: C, 66.94; H, 6.20; N, 11.59. $C_{26}H_{28}N_4O_4$; $0.2H_2O$; $0.3(CH_3CH_2)_2O$ requires C, 67.17; H, 6.51; N, 11.52%.

EXAMPLE 258 & EXAMPLE 259

Compound from example 18 was separated via chiral HPLC into its two enantiomers, using a Chiralpak AD250 20 mm column, in 50% hexane 50% isopropylalcohol, at 220 nm over 40 min at a flow rate of 10 mL/min. Enantiomeric excesses were determined by HPLC analysis using a Chiralpak AD250 4.6 mm column, in 50% hexane 50% isopropylalcohol, at 220 nm over 30 min at a flow rate of 1 mL/min

EXAMPLE 258

(R or S)-2-Amino-N-[carbamoyl-[(3-methoxyphenyl)-methyl]-4,6-dimethyl-N-(4-methyl-benzyl)-nicotinamide

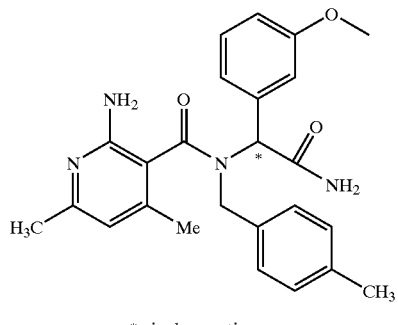

* single enantiomer

Enantiomer 1: retention time 14.87 min, >99% ee
LRMS: m/z ($ES^+$) 433 [$MH^+$], 85%; 455 [$MNa^+$], 100%

EXAMPLE 259

(R or S)-2-Amino-N-[carbamoyl-{(3-methoxyphenyl)-methyl}]-4,6-dimethyl-N-(4-methyl-benzyl)-nicotinamide

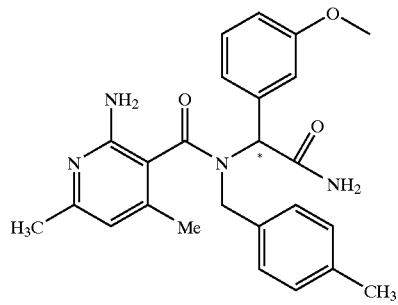

* single enantiomer

Enantiomer 2: retention time 20.20 min, 98.89 ee
LRMS: m/z ($ES^+$) 433 [$MH^+$], 95%; 455 [$MNa^+$], 100%

Preparation 1

2-Methylamino-nicotinic acid

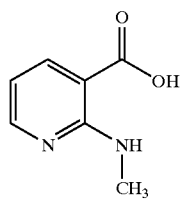

Methylamine hydrochloride (8.6 g, 128 mmol) was added portionwise to a mixture of 2-chloronicotinic acid (10.0 g, 64 mmol), potassium carbonate (35.4 g, 256 mmol) and copper (I) bromide (920 mg, 6.4 mmol) in N,N-dimethylformamide (100 ml), and the reaction heated at 100° C. for 18 hours, then cooled. The resulting precipitate was removed by filtration, washing through with additional methanol and the filtrate evaporated under reduced pressure.

The residue was redissolved in 2N sodium hydroxide solution (200 ml), washed with diethyl ether (4×80 ml), then the pH of the aqueous solution adjusted to 6, using concentrated hydrochloric acid. This aqueous solution was evaporated under reduced pressure, the residue dissolved in methanol, poly(4-vinylpyridine), 2% cross-linked (5 g) was added, and the mixture stirred at room temperature for 18 hours. The resin was removed by filtration, and the procedure then repeated. The solution was evaporated under reduced pressure, and the solid recrystallised from ethanol, to afford the title compound, 5.2 g.

$^1$H-nmr (DMSO-d$_6$, 270 MHz) δ 2.91 (s, 3H), 6.50 (dd, 1H), 8.02 (dd, 1H), 8.13 (m, 1H), 8.37 (m, 1H).

LRMS: m/z (ES$^+$) 153 [MH$^+$]

Preparation 2

2-Ethylamino-nicotinic acid

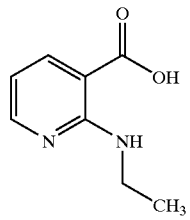

Potassium carbonate (9.21 g, 66.6 mmol) was added to a mixture of 2-chloronicotinic acid (5.0 g, 31.7 mol), ethylamine hydrochloride (5.18 g, 63.4 mmol) and copper (I) bromide (450 mg, 3.17 mmol) in N,N-dimethylformamide (50 ml), and the reaction heated at 100° C. for 1.5 hours, then cooled. The resulting solid was removed by filtration, and the filtrate evaporated under reduced pressure. The residual blue/green solid was triturated with acetone, and the resulting solid filtered off and dried in vacuo to afford the title compound.

The filtrate was evaporated under reduced pressure, the residue triturated with diethyl ether and the solid filtered and dried in vacuo, to afford additional product, 2.2 g in total.

Preparation 3

2-Benzylamino-nicotinic Acid

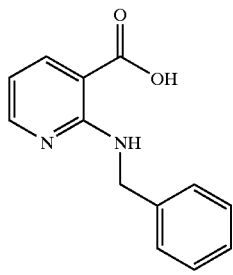

Potassium carbonate (4.82 g, 34.9 mmol) was added to a mixture of 2-chloronicotinic acid (5.0 g, 31.7 mol), benzylamine (3.47 ml, 31.7 mmol) and copper (I) bromide (450 mg, 3.17 mmol) in N,N-dimethylformamide (50 ml), and the reaction heated at 100° C. for 2 hours, then cooled. The resulting solid was filtered off and the filtrate evaporated under reduced pressure. The residue was partitioned between 4N sodium hydroxide solution (25 ml) and dichloromethane (25 ml) and the layers separated. The organic solution was extracted with water (2×), and the combined aqueous solutions, neutralised using concentrated hydrochloric acid. The resulting solid was filtered off, washed with cold water and dried in vacuo at 50° C., to afford the title compound, 1.6 g.

$^1$H-nmr (DMSOd$_6$, 300 MHz) □: 4.69 (d, 2H), 6.62 (dd, 1H), 7.31 (m, 5H), 8.10 (dd, 1H), 8.24 (dd, 1H), 8.48 (bs, 1H).

Preparation 4

2-{[-3-(4-Morphonlinyl)propyl]amino}nicotinic Acid

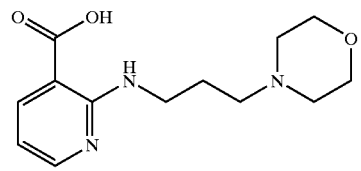

3-(4-Morpholino)-1-propylamine (9.23 g, 40 mmol) was added to a solution of 2-chloronicotininc acid (5 g, 32 mmol), potassium carbonate (4.42 g, 3 mmol) and copper (I) bromide (460 mg, 3.2 mmol) in N,N-dimethylformamide, and the mixture stirred at 110° C. for 21 hours. The cooled mixture was filtered and the filtrate concentrated under reduced pressure, and the residue azeotroped with toluene.

The residue was dissolved in methanol (40 ml), and poly(4-vinylpyridine) 2% cross-linked was added, the mixture stirred for an hour, then filtered. The filtrate was concentrated under reduced pressure, the residue dissolved in a minimum volume of dichloromethane, and added dropwise into diethyl ether (250 ml), yielding an oil. The solvent was decanted off, the oil re-dissolved in a minimum volume of dichloromethane and again added dropwise to diethyl ether. The resulting precipitate was filtered and dried to afford the title compound, 4.3 g.

$^1$H-nmr (D$_2$O, 270 MHz) δ: 1.86–1.97 (m, 2H), 2.74–2.92 (m, 6H), 3.41 (m, 2H), 3.83 (m, 4H), 6.67 (m, 1H), 8.01 (d, 1H), 8.06 (d, 1H).

LRMS: m/z (TSP$^+$) 266 [MH$^+$]

Preparation 5

2-Fluoro-5-formylbenzonitrile

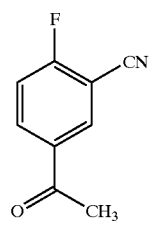

Iso-propyl magnesium bromide (18 ml, 1M in tetrahydrofuran, 18 mmol) was added dropwise to an ice-cooled solution of 5-bromo-2-fluorobenzonitrile (3 g, 15.1 mmol) in tetrahydrofuran (25 ml), and once addition was complete, the mixture was allowed to warm to room temperature and stirred for a further 2 hours. N,N-Dimethylformamide (3.5 ml, 45.2 mmol) was added and the reaction stirred for 3 hours. Water was added and the mixture extracted with ethyl acetate (3×). The combined organic extracts were washed with 6% aqueous magnesium sulphate solution, and brine, then dried (Na$_2$SO$_4$) and concentrated under reduced pressure. The product was purified by column chromatography on silica gel using an elution gradient of ethyl acetate:hexane (10:90 to 20:80) to afford the title compound as a light yellow solid, 1.01 g.

$^1$H-nmr (CDCl$_3$) δ: 3.27 (s, 3H), 6.83 (d, 1H), 7.83 (dd, 1H), 7.94 (d, 1H), 9.72 (s, 1H).

Preparation 6

(4-Isocyano-cyclohex-3-enyl)-benzene

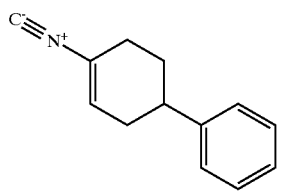

Potassium tert-butoxide (34.3 g, 306 mmol) was added portionwise to a solution of 4-phenyl-1-formamidocyclohexene (13.6 g, 68 mmol) (Biiorg. Med. Chem; 8; 6; 2000; 1343) in tert-butanol (150 ml), and the mixture stirred for 2 hours, with sufficient heating to ensure solution. Phosphorous oxychloride (7.82 g, 51 mmol) was added dropwise, with cooling of the reaction vessel, and once additon was complete, the reaction was stirred at room temperature for 24 hours. TLC analysis showed starting material remaining, so additional potassium tert-butoxide (3.8 g, 34 mmol) and phosphorous oxychloride (1.57 ml, 17 mmol) were added, and the reaction stirred for a further 45 minutes. The mixture was concentrated under reduced pressure, the residue poured into brine (500 ml) and extracted with dichloromethane (100 ml, 3×50 ml). The combined organic solutions were washed with water (100 ml), brine (200 ml), dried (Na$_2$SO$_4$) and evaporated under reduced pressure. The crude product was purified by column chromatography on silica gel using hexane:ethyl acetate (90:10) as eluant to afford the title compound, 5.8 g.

$^1$H nmr (CDCl$_3$, 270 MHz) δ: 1.80–1.90 (m, 1H), 1.97–2.08 (m, 1H), 2.23–2.47 μm, 4H), 2.72–2.82 (m, 1H), 6.11 (s, 1H), 7.17–7.34 (m, 5H).

Preparation 7

Methyl 3-amino-3-(3-methoxyphenyl)propanoate

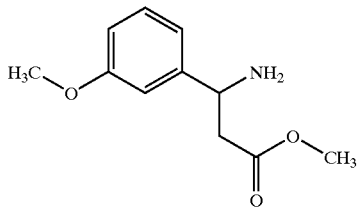

A solution of β-amino-3-methoxy-benzenepropanoic acid (WO 0041469) (9.38 g, 52 mmol) in concentrated hydrochloric acid (10 ml) and methanol (115 ml), was heated under reflux for 7 hours, then cooled. The reaction was evaporated under reduced pressure, and the residue partitioned between ethyl acetate (300 ml) and 1N sodium hydroxide solution (300 ml). The layers were separated, and the organic phase evaporated under reduced pressure to afford the title compound as a colourless oil, 8.8 g.

$^1$H nmr (CDCl$_3$, 400 MHz) δ: 2.77 (m, 4H), 3.68 (s, 3H), 3.80 (s, 3H), 4.42 (t, 1H), 6.80 (m, 1H), 6.96 (m, 2H), 7.24 (m, 1H).

LRMS: m/z (ES$^+$) 232 [MNa$^+$]

Preparation 8 tert-Butyl(1S)-3-amino-3-oxo-1-phenylpropylcarbamate

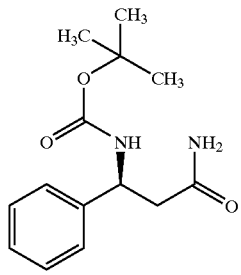

A mixture of 1-hydroxybenzotriazole hydrate (3.46 g, 25.6 mmol), 1-(3-dimethylaminopropyl)-3-ethylcarbodiimide hydrochloride (4.91 g, 25.6 mmol), and (S)-N-tert-butoxycarbonyl-3-amino-3-phenylpropanoic acid (6.80 g, 25.6 mmol) in dichloromethane (250 ml) was stirred at room temperature for 1 hour. 0.88 Ammonia (20 ml) was added and the mixture stirred at room temperature for a further 18 hours. The resulting solid was filtered off and washed with sodium bicarbonate solution, then water and dried under vacuum at 50° C. to afford the title compound, 6.78 g.

$^1$H nmr (CDCl$_3$, 400 MHz) 8:1.42 (s, 9H), 2.78 (s, 2H), 5.04 (m, 1H), 5.35 (s, 1H), 5.74 (s, 1H), 5.84 (s, 1H), 7.24 (m, 5H).

LRMS: m/z (ES$^+$) 287 [MNa$^+$]

$[α]_D$=−38.73° (c=0.25, methanol)

Preparation 9

(3S)-3-Amino-3-phenylpropanamide

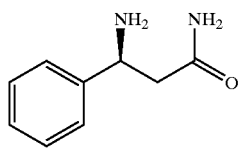

4M Hydrochloric acid in dioxan (50 ml) was added to a solution of the protected amine from preparation 8 (6.50 g, 24.6 mmol) in methanol (20 ml), and the solution stirred at room temperature for 18 hours. The solution was evaporated under reduced pressure to give a white solid. This was dissolved in water (50 ml), 1M sodium hydroxide (27 ml, 27 mmol) added and the solution allowed to stir for 18 hours at room temperature. The aqueous solution was extracted with dichloromethane and then ethyl acetate and the combined organic extracts were dried (Na$_2$SO$_4$) and evaporated under reduced pressure to afford the title compound as a white solid, 1.32 g.

¹H nmr (DMSOd₆, 400 MHz) δ: 2.32 (d, 3H), 4.18 (t, 2H), 6.78 (s, 1H), 7.18 (m, 1H), 7.22–7.40 (m, 5H).
LRMS: m/z (APCI) 165 [MH⁺]

Preparation 10

Methyl 3-(3-methoxyphenyl]-3-[(4-methylbenzyl)amino]propanoate

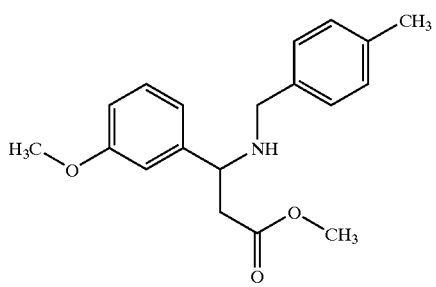

A mixture of the amine from preparation 7 (8.8 g, 42 mmol), p-tolualdehyde (5.10 g, 42 mmol), acetic acid (1 ml), and sodium triacetoxyborohydride (11.57 g, 55 mmol) in dichloromethane (500 ml) was stirred at room temperature for 18 hours. 2N Hydrochloric acid (50 ml) was added, and the solution stirred for a further 30 minutes. The reaction was basified using sodium bicarbonate solution, the phases separated, and the aqueous layer extracted with dichloromethane (500 ml). The combined organic solutions were dried (Na₂SO₄) and evaporated under reduced pressure to give an oil. This was purified by column chromatography on silica gel using an elution gradient of dichloromethane:methanol: 0.88 ammonia (100:0:0 to 97.5:2.5:0.25) to afford the title compound, 7.68 g.

¹H nmr(CDCl₃, 400 MHz) δ: 2.36 (s, 3H), 2.70 (m, 1H), 2.83 (m, 1H), 3.54 (d, 1H), 3.63 (m, 4H), 3.82 (s, 3H), 4.12 (m, 1H), 6.82 (m, 1H), 6.99 (m, 2H), 7.12 (d, 2H), 7.18 (d, 2H), 7.24 (m, 1H).
LRMS: m/z (ES⁺) 336 [MNa⁺]

Preparation 11

(3S)-3-[(4-Methylbenzyl)amino]-3-phenylpropanamide

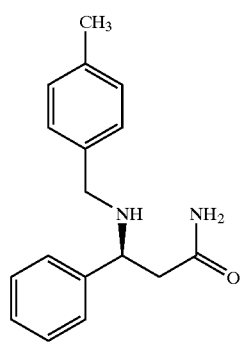

The title compound was obtained in 62% yield from p-tolualdehyde and the amine from preparation 9, following the procedure decribed in preparation 10.

¹H nmr(CDCl₃, 400 MHz) δ: 2.38 (s, 3H), 2.51 (dd, 1H), 2.62 (dd, 1H), 3.58 (d, 1H), 3.63 (m, 4H), 4.03 (dd, 1H), 5.40 (s, 1H), 7.20–7.40 (m, 6H)
LRMS: m/z (ES⁺) 269 [MH⁺].

Preparation 12

Methyl 3-(3-methoxyphenyl)-3-{(4-methylbenzyl)[(4-methyl-3-pyridinyl)carbonyl]amino}propanoate

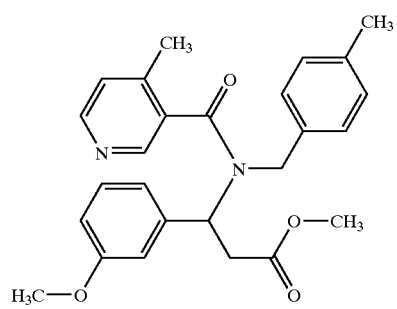

Oxalyl chloride (731 mg, 5.76 mmol) and N,N-dimethylformamide (1 drop) were added to a solution of 4-methylnicotininc acid (500 mg, 2.88 mmol) in dichloromethane (25 ml) and the solution stirred at room temperature for 4 hours.

The reaction was evaporated under reduced pressure, to give 4-methyl-nicotinoyl chloride.

A solution of the freshly prepared acid chloride, the amine from preparation 10 (400 mg, 1.28 mmol), and N-ethyldiisopropylamine (0.67 ml, 3.84 mmol) in dichloromethane (50 ml) was stirred at room temperature for 18 hours. The reaction was washed with sodium bicarbonate solution (50 ml), water (50 ml) then brine (50 ml), dried (Na₂SO₄) and evaporated under reduced pressure. The residue was purified by column chromatography on silica gel using an eluton gradient of dichloromethane:methanol: 0.88 ammonia (100:0:0 to 97.5:2.5:0.25) to afford the title compound, 289 mg.

LRMS: m/z (ES⁺) 433 [MH⁺]

Preparation 13

3-(3-Methoxyphenyl)-N-(4-methylbenzyl)-N-[(4-methyl-3-pyridinyl)carbonyl]-☐-alanine

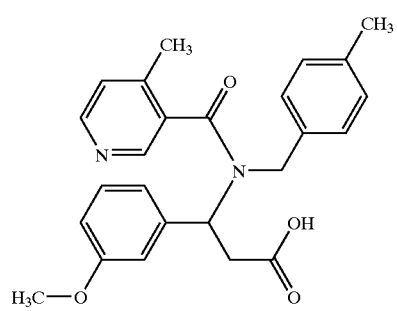

Lithium hydroxide (30 mg, 0.74 mmol) was added to a solution of the ester from preparation 12 (289 mg, 0.67 mmol) in water (10 ml) and tetrahydrofuran (10 ml), and the mixture stirred at room temperature for 18 hours. The solution was concentrated under reduced pressure and the aqueous residue washed with ethyl acetate (20 ml). The aqueous solution was acidified to pH 5 using 2N hydrochloric acid, then extracted with ethyl acetate (20 ml). This solution was dried (Na₂SO₄) and evaporated under reduced pressure. The residue was purified by column chromatography on silica gel using dichloromethane:methanol: 0.88 ammonia (100:0:0 to 97.5:2.5:0.25) to afford the title compound, 176 mg.

HRMS: m/z (ES$^+$) 418.2117 [MH$^+$], C$_{25}$H$_{27}$N$_3$O$_3$ requires 418.2125.

Preparation 14

5-Chloro-2-(2-t-butoxycarbonylaminoethylamino-N-[2-amino-1-{1,4-benzodioxan-6-yl}-2-oxoethyl]-N-(4-methylbenzyl)pyrimidine-4-carboxamide

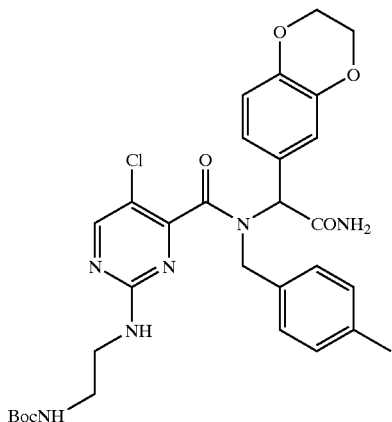

The title compound was made from the sulfone from example 243 and N-Boc-ethylenediamine (commercially available from Aldrich) using the method of example 244 and was used immediately in the next step Preparation 15

Methyl-2-keto-3-methyl-4-dimethylaminobut-3-enoate

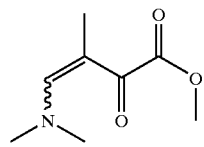

Methyl-2-ketobutyrate (5 g, 43 mmol) was added at ambient temperature to dimethylformamide dimethyl acetal (5.13 g, 43 mmol, 5.72 ml). The solution was stirred overnight under nitrogen and then the volatile components were removed in vacuo at 40° C. The yellow residue was used without further purification.

$^1$Hnmr (CDCl$_3$, 400 MHz) δ: 2.0 (s, 3H), 3.18 (s, 6H), 3.8 (s, 3H), 7.05–7.15 (br s, 1H)

LRMS: m/z (APCI$^+$) 172 [MH$^+$]

Preparation 16

Methyl-5-methyl-2-methylthiopyrimidine-4-carboxylate

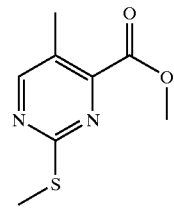

Sodium metal (1.05 g, 45.5 mmol) was added to methanol (40 ml) at ambient temperature. After dissolution of the metal, S-methylisothiouronium sulfate (6.34 g, 22.8 mmol) was added in one portion, followed by methyl-2-keto-3-methyl-4-dimethylaminobut-3-enoate (3.9 g, 22.8 mmol, preparation 15) dropwise as a solution in 5 ml of methanol. The reaction was stirred at ambient temperature for 1 hr and then heated to 50° C. for 3 hrs. After cooling, the solvent was evaporated. The residue was partitioned between ethyl acetate (50 ml) and water (30 ml). The organic phase was separated and washed with brine (20 ml), dried over MgSO$_4$, filtered and evaporated. The residue was purified by chromatography on silica using a gradient of ethyl acetate/pentane as eluent, starting with 95/5 and increasing to give the title compound as a solid, 0.9 g, (20%).

$^1$Hnmr (CDCl$_3$, 400 MHz) δ: 2.4 (s, 3H), 2.58 (s, 3H), 3.98 (s, 3H), 8.50 (s, 1H)

LRMS m/z (APCI$^+$) 199 [MH$^+$]

Preparation 17

5-methyl-2-methylthiopyrimidine-4-carboxylic Acid

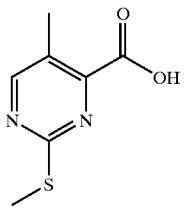

Sodium hydroxide (0.37 g, 4.6 mmol) was added dropwise as a solution in water (2 ml) to a solution of the ester, from preparation 16, in methanol (5 ml) at ambient temperature. After 20 minutes the reaction mixture was acidified with 2M HCl and the methanol evaporated. The resulting aqueous suspension was extracted with CH$_2$Cl$_2$ (3×10 ml). The combined extracts were dried over MgSO$_4$, filtered and evaporated. The solid residue was broken up in ether and filtered to give the title compound as a solid, 0.57 g, (67%).

$^1$Hnmr (CDCl$_3$, 400 MHz) δ: 2.25 (s, 3H), 2.45 (s, 3H), 8.35 (s, 1H)

LRMS: m/z (APCI$^+$) 185 [MH$^+$]

What is claimed is:

1. A compound of formula (I)

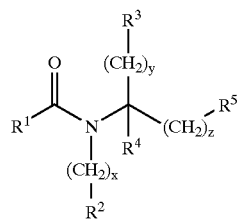

wherein:

$R^1$ is selected from:
a) phenyl, which is optionally substituted by 1–3 groups each independently selected from $C_1$-$C_6$ alkyl, $CF_3$, halo, CN, $NR^7R^8$, $SO_2R^6$ and $OC_1$-$C_6$ alkyl, and
b) Aromatic Heterocycle, wherein said Aromatic Heterocycle is selected from pyridyl, pyrazinyl, pyrimidinyl, quinolinyl, quinoxalinyl, isoxazolyl and pyrazolyl, each aromatic heterocycle optionally substituted by 1–3 groups each independently selected from $C_1$-$C_6$ alkyl, $SR^6$, $SO_2R^6$, $NH_2$, $CF_3$, halo, OH, $OC_1$-$C_6$ alkyl, $NR^7R^8$ wherein $R^8$ may be optionally substituted by $NH_2$, phenyl or Heterocycle, and OPh wherein Ph may be optionally substituted by 1–3 groups each independently selected from halo and $C_1$-$C_6$ alkyl;

$R^2$ is selected from:
a) phenyl, which is optionally substituted by methyl, fluoro, chloro, methoxy, $CF_3$ or $SO_2CH_3$,
b) pyrazolyl, which is optionally substituted by methyl, and
c) $C(O)N(CH_3)_2$;

$R^3$ is selected from:
a) phenyl, said phenyl being optionally fused to Heterocycle and said phenyl or said fused phenyl being optionally substituted by 1–3 groups each independently selected from $C_1$-$C_6$ alkyl, halo, CN and $OC_1$-$C_6$alkyl,
b) $R^5$,
c) cyclopropyl, cyclobutyl, cyclopentyl or cyclohexyl, which is optionally substituted by $C_1$-$C_6$ alkyl; and
d) Aromatic Heterocycle, wherein said Aromatic Heterocycle may be defined as a 5–6 membered aromatic heterocycle containing 1 or 2 nitrogen atoms, said ring optionally fused with a phenyl or a 3–8 membered cycloalkyl group.

$R^4$ is H;
$R^5$ is $CONH_2R^6$;
$R^6$ is methyl;
$R^7$ is hydrogen or $C_1$-$C_6$ alkyl;
$R^8$ is $C_1$-$C_6$ alkyl;
or $NR^7R^8$ forms a monocyclic saturated ring system containing between 3 and 7 ring atoms;
x is 1;
y is 0; and
z is 0 or 1
wherein:
Aromatic Heterocycle may be defined as a 5–6 membered aromatic heterocycle containing 1–4 heteroatoms each independently selected from N, O and S, said ring optionally fused with a phenyl or a 3–8 membered cycloalkyl group;
Heterocycle is a 5–8 membered saturated or partially saturated ring containing 1–3 heteroatoms each independently selected from N. O and S, said ring optionally fused with phenyl;

a tautomer thereof or a pharmaceutically acceptable salt, solvate or polymorph of said compound or tautomer.

2. A compound according to claim 1 wherein $R^1$ is selected from:
a) phenyl, which is optionally substituted by 1–3 groups each independently selected from $C_1$-$C_6$ alkyl, $CF_3$, halo, CN, $NR^7R^8$, $SO_2R^6$ and $OC_1$-$C_6$ alkyl, and
b) Aromatic Heterocycle, wherein said Aromatic Heterocycle is selected from:
  i) pyridyl, which is optionally substituted by 1–3 groups each independently selected from $C_1$-$C_8$alkyl, $SO_2R^5$, $NH_2$, $CF_3$, CN, halo, OH, $OC_1$-$C_6$ alkyl, $NR^7R^8$ wherein $R^8$ may be optionally substituted by $NH_2$, phenyl or Heterocycle, and OPh wherein Ph may be optionally substituted by 1–3 groups each independently selected from halo and $C_1$-$C_6$ alkyl;
  ii) pyrimidinyl, which is optionally substituted by 1–3 groups each independently selected from $C_1$-$C_6$ alkyl, $SO_2R^5$, $NH_2$, $CF_3$ CN, halo, OH, $OC_1$-$C_6$ alkyl, $NR^7R^8$ wherein $R^8$ may be optionally substituted by $NH_2$, phenyl or Heterocycle, and OPh wherein Ph may be optionally substituted by 1–3 groups each independently selected from halo and $C_1$–$C_6$ alkyl;
  iii) pyrazinyl, which is optionally substituted by 1–3 groups each independently selected from $C_1$-$C_6$ alkyl, $NH_2$, $SR^6$ and halo;
  iv) quinolinyl;
  v) quinoxalinyl, which is optionally substituted by OH;
  vi) isoxazolyl, which is optionally substituted by 1–3 groups each independently selected from: $C_1$-$C_6$ alkyl; and
  vii) pyrazole;

$R^3$ is selected from:
a) phenyl, said phenyl being optionally fused to 1,4-dioxan and said phenyl or said fused phenyl being optionally substituted by 1–3 groups each independently selected from $C_1$-$C_6$ alkyl, halo, CN and $OC_1$-$C_6$ alkyl;
b) $R^6$,
c) cyclopropyl, which is optionally substituted by $C_1$-$C_6$ alkyl; and
d) Aromatic Heterocycle, wherein said Aromatic Heterocycle is selected from pyrazolyl or pyridyl, both optionally substituted by $C_1$-$C_6$ alkyl;

and z is 0.

3. A compound according to any one of claims 1 or 2 wherein $R^1$ is phenyl, 2- or 3-pyridyl or 2,4-pyrimidinyl, said moieties being optionally substituted by 1–3 groups each independently selected from $C_1$-$C_6$ alkyl, halo, $OC_1$-$C_6$ alky), CN, $SO_2R^6$, $NHR_7$, $NHCH_2CH_2NH_2$ and $CF_3$.

4. A compound according to claim 3 wherein $R^1$ is phenyl, 2- or 3-pyridyl or 2,4-pyrimidinyl, said moieties being optionally substituted by 1–3 groups each independently selected from methyl, fluoro, chloro, methoxy, ethoxy, n-propoxy, CN, $SO_2CH_3$, $NH_2$. $NHCH_3$, $NHCH_2CH_2NH_2$, and $CF_3$.

5. A compound according to claim 4 wherein $R^2$ is phenyl, para-fluorophenyl, para-chlorophenyl, para-methylphenyl, 2,5-dimethylphenyl, o-methylphenyl and para-methoxyphenyl.

6. A compound according to claim 5 wherein $R^3$ is selected from:

a) phenyl, said phenyl being optionally fused to 1,4-dioxan and said phenyl or said fused phenyl being optionally substituted by 1–2 groups each independently selected from methyl, methoxy, ethoxy, fluoro, chloro and CN;

b) isopropyl;

c) cyclopropyl; and d) pyrazolyl and pyridyl, both optionally substituted by methyl.

7. A compound according to claim 6 wherein $R^3$ is 3-methylphenyl or 1,4-benzodioxanyl.

8. A compound according to claim 7 wherein $R^5$ is $CONH_2$.

9. A compound according to claim 1 selected from:
2-Amino-N-[2-amino-1-(2-methylphenyl)-2-oxoethyl]-N-(4- chlorobenzyl)nicotinamide,
N-[2-Amino-1-(3-methoxyphenyl)-2-oxoethyl]-4-cyano-N-(4-methylbenzyl)benzamide,
N-[3-Amino-1-(3-methoxyphenyl)-3-oxoethyl]-4-methyl-N-(4-methylbenzyl)nicotinamide,
2-Amino-N-[(1S)-3-amino-3-oxo-1-phenylpropyl]-N-(4-methylbenzyl)nicotinamide,
5-Chloro-2-methylthio-N-[2-amino-1-(1,4-benzodioxan-6-yl)-2-oxoethyl]-N-(4-methylbenzyl)pyrimidine-4-carboxamide,
5-Chloro-2-amino-N-[2-amino-1-(1,4-benzodioxan-6-yl)-2-oxoethyl]-N-(4-methylbenzyl)pyrimidine-4-carboxamide, and
2-Amino-N-[carbamoyl-(2,3-dihydro-benzo[1,4]dioxin-6-yl)-methyl]-4,6-dimethylN-(4-methyl-benzyl)-nicotinamide;

and tautomers thereof and pharmaceutically acceptable salts, solvates and poly of said compound or tautomer.

10. A pharmaceutical composition comprising a compound of claim 1 or pharmaceutically acceptable salts, solvates or polymorphs thereof, and a pharmaceutically acceptable diluent or carrier.

11. A method of treatment of a disorder or condition where inhibition of Oxytocin is known, or can be: shown, to produce a beneficial effect, in a mammal, comprising administering to said mammal a therapeutically effective amount of a compound of claim 1.

12. A method according to claim 11 wherein the disorder or condition is selected from sexual dysfunction (including premature ejaculation), preterm labour, complications in labor, appetite and feeding disorders, obesity, benign prostatic hyperplasia, premature birth, dysmenorrhoea, congestive heart failure, arterial hypertension, liver cirrhosis, nephrotic hypertension, occular hypertension, obsessive compulsive disorder and neuropsychiatric disorders.

13. A method according to claim 12, wherein the disorder or condition is premature ejaculation.

* * * * *